(12) United States Patent
Miyake et al.

(10) Patent No.: US 10,347,844 B2
(45) Date of Patent: Jul. 9, 2019

(54) MATERIAL FOR ORGANIC ELECTROLUMINESCENT DEVICE AND ORGANIC ELECTROLUMINESCENT DEVICE USING THE SAME

(71) Applicant: Samsung Display Co., Ltd., Yongin-si, Gyeonggi-do (KR)

(72) Inventors: Hideo Miyake, Yokohama (JP); Ichinori Takada, Yokohama (JP); Hiromi Nakano, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 14/925,960

(22) Filed: Oct. 28, 2015

(65) Prior Publication Data

US 2016/0133849 A1 May 12, 2016

(30) Foreign Application Priority Data

Nov. 7, 2014 (JP) .................................. 2014-227220

(51) Int. Cl.
| | | |
|---|---|---|
| *C07D 307/91* | (2006.01) | |
| *H01L 51/00* | (2006.01) | |
| *C09K 11/02* | (2006.01) | |
| *H01L 51/50* | (2006.01) | |

(52) U.S. Cl.
CPC ........ *H01L 51/0061* (2013.01); *C07D 307/91* (2013.01); *C09K 11/025* (2013.01); *H01L 51/006* (2013.01); *H01L 51/0073* (2013.01); *H01L 51/5012* (2013.01); *H01L 51/5056* (2013.01)

(58) Field of Classification Search
None
See application file for complete search history.

(56) References Cited

U.S. PATENT DOCUMENTS

| | | | | |
|---|---|---|---|---|
| 8,431,250 B2* | 4/2013 | Mizuki | ................ | C07D 307/91 257/40 |
| 8,580,980 B2 | 11/2013 | Osaka et al. | | |
| 9,972,787 B2 | 5/2018 | Miyake et al. | | |
| 2010/0314615 A1* | 12/2010 | Mizuki | ................ | C07D 307/91 257/40 |
| 2012/0065530 A1 | 3/2012 | Masumoto | | |
| 2013/0264558 A1 | 10/2013 | Matsuki et al. | | |
| 2013/0299793 A1 | 11/2013 | Chen et al. | | |
| 2015/0021555 A1* | 1/2015 | Kwong | ................ | H01L 51/0061 257/40 |
| 2016/0093810 A1* | 3/2016 | Miyake | ................ | H01L 51/0052 548/440 |

(Continued)

FOREIGN PATENT DOCUMENTS

| | | |
|---|---|---|
| EP | 2532655 A1 | 12/2012 |
| EP | 3101016 A1 | 12/2016 |

(Continued)

OTHER PUBLICATIONS

Periodic Table, http://www.chem.qmul.ac.uk/iupac/AtWt/table.html, accessed May 24, 2017.*

*Primary Examiner* — Noble E Jarrell
(74) *Attorney, Agent, or Firm* — Lewis Roca Rothgerber Christie LLP

(57) ABSTRACT

A novel and improved material for an organic electroluminescent device includes at least one monoamine compound represented by any one of the following Formulae I to III:

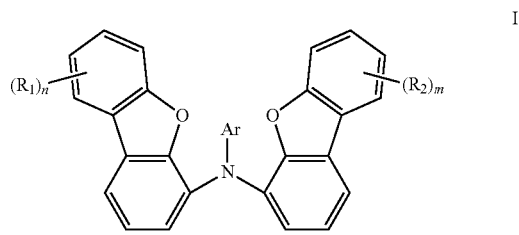

I

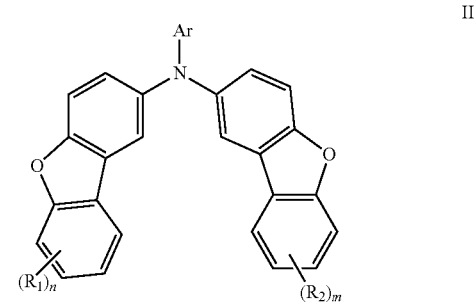

II

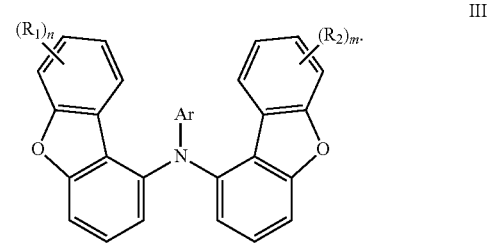

III

In Formulae I to III, Ar is a substituted or unsubstituted aryl group having 6 to 50 carbon atoms for forming a ring. The organic electroluminescent device including the material may have improved emission life.

11 Claims, 2 Drawing Sheets

(56) References Cited

U.S. PATENT DOCUMENTS

| | | | |
|---|---|---|---|
| 2016/0126469 A1* | 5/2016 | Nakano | H01L 51/0061 257/40 |
| 2016/0254456 A1* | 9/2016 | Heil | C07C 17/263 257/40 |
| 2016/0329492 A1 | 11/2016 | Funahashi et al. | |
| 2017/0317289 A1 | 11/2017 | Lee et al. | |

FOREIGN PATENT DOCUMENTS

| | | | | |
|---|---|---|---|---|
| JP | 2008-21687 A | | 1/2008 | |
| JP | 2012-140418 A | | 7/2012 | |
| JP | 2012073548 | * | 3/2013 | C07D 307/91 |
| JP | 2016-66723 A | | 4/2016 | |
| JP | 6157718 B2 | | 7/2017 | |
| KR | 2014-111671 | * | 8/2014 | |
| KR | 2014-139143 | * | 10/2014 | |
| KR | 2016024625 | * | 3/2016 | C09K 11/06 |
| WO | 2010002848 | * | 1/2010 | C09K 11/06 |
| WO | WO 2010/061824 A1 | | 6/2010 | |
| WO | WO 2010/114017 A1 | | 10/2010 | |
| WO | WO 2011/059099 A1 | | 5/2011 | |
| WO | WO 2011/090149 A1 | | 7/2011 | |
| WO | WO 2012/034627 A1 | | 3/2012 | |
| WO | WO 2012/039534 A1 | | 3/2012 | |
| WO | WO 2012/085803 A1 | | 6/2012 | |
| WO | WO 2013/039184 A1 | | 3/2013 | |
| WO | WO 2014/034791 A1 | | 3/2014 | |
| WO | WO 2014/034795 A1 | | 3/2014 | |
| WO | 2014111269 | * | 7/2014 | C07C 13/00 |
| WO | WO 2016060332 | * | 4/2016 | C09K 11/06 |

* cited by examiner

MATERIAL FOR ORGANIC ELECTROLUMINESCENT DEVICE AND ORGANIC ELECTROLUMINESCENT DEVICE USING THE SAME

CROSS-REFERENCE TO RELATED APPLICATION

This patent application claims priority to and the benefit of Japanese Patent Application No. 2014-227220, filed on Nov. 7, 2014, the entire content of which is hereby incorporated by reference.

BACKGROUND

One or more aspects of embodiments of the present disclosure herein relate to a material for an organic electroluminescent device and an organic electroluminescent device using the same.

Recently, the development of an organic electroluminescent display and an organic electroluminescent device (a self luminescent device used in the organic electroluminescent display) has been actively conducted.

An organic electroluminescent device may include, for example, a structure including an anode, a hole transport layer positioned on the anode, an emission layer positioned on the hole transport layer, an electron transport layer positioned on the emission layer and a cathode positioned on the electron transport layer.

In the organic electroluminescent device as described above, holes and electrons injected from the anode and the cathode may recombine in the emission layer to generate excitons, and the excitons thus generated may emit light via transition to a ground state. As a hole transport material used in the hole transport layer, a monoamine compound including a dibenzofuranyl group has been used. However, the emission life of the organic electroluminescent device including such monoamine compound as the hole transport material may not be satisfactory.

SUMMARY

One or more aspects of embodiments of the present disclosure are directed toward a novel and improved material for an organic electroluminescent device, which may improve the emission life of the organic electroluminescent device and an organic electroluminescent display using the same.

One or more embodiments of the present disclosure provide a material for an organic electroluminescent device including at least one monoamine compound represented by any one of the following Formulae I to III:

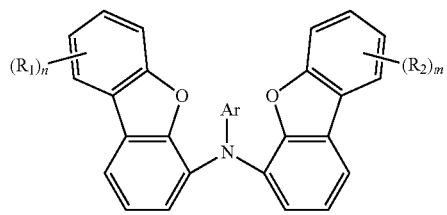

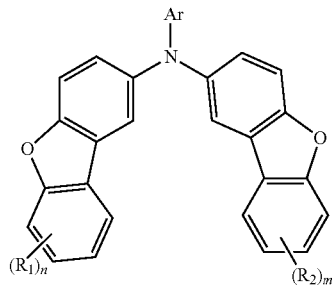

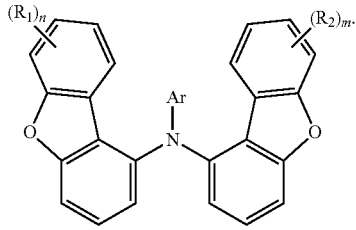

In the above Formulae I to III, Ar may be a substituted or unsubstituted aryl group having 6 to 50 carbon atoms for forming a ring; $R_1$ and $R_2$ may be each independently selected from a hydrogen atom, a halogen atom, an alkyl group having 1 to 15 carbon atoms, a substituted or unsubstituted aryl group having 6 to 30 carbon atoms for forming a ring, and a substituted or unsubstituted heteroaryl group having 1 to 30 carbon atoms for forming a ring; and n and m may be each independently an integer selected from 1 to 4.

According to one or more embodiments of the present disclosure, the emission life of the organic electroluminescent device may be improved.

In some embodiments, Ar may be selected from a substituted or unsubstituted phenyl group, a substituted or unsubstituted naphthyl group, a substituted or unsubstituted anthracenyl group, a substituted or unsubstituted phenanthryl group, a substituted or unsubstituted perylenyl group, a substituted or unsubstituted tetracenyl group, a substituted or unsubstituted biphenyl group, a substituted or unsubstituted terphenyl group, a substituted or unsubstituted naphthylphenyl group, a substituted or unsubstituted biphenylenyl group, a substituted or unsubstituted indenyl group, and a substituted or unsubstituted fluoranthenyl group.

According to one or more embodiments of the present disclosure, the emission life of the organic electroluminescent device may be improved.

In some embodiments, Ar may be selected from a substituted or unsubstituted phenanthrenyl group, a substituted or unsubstituted terphenyl group, and a substituted or unsubstituted naphthylphenyl group.

According to one or more embodiments of the present disclosure, the emission life of the organic electroluminescent device may be improved.

In some embodiments, Ar may include the substituted or unsubstituted phenanthrenyl group.

According to one or more embodiments of the present disclosure, the emission life of the organic electroluminescent device may be improved.

In some embodiments of the present disclosure, an organic electroluminescent device includes the above-described material for an electroluminescent device.

According to one or more embodiments of the present disclosure, the emission life of the organic electroluminescent device may be improved.

In some embodiments, the material for an organic electroluminescent device may be included in a hole transport layer.

According to one or more embodiments of the present disclosure, the emission life of the organic electroluminescent device may be improved.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
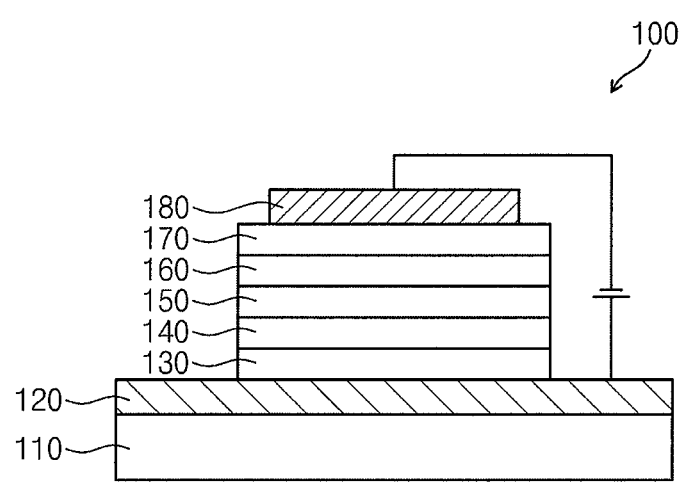
FIG. 1 is a cross-sectional view illustrating the schematic configuration of an organic electroluminescent device according to one or more embodiments of the present disclosure.

Hereinafter, embodiments of the present disclosure will be described in more detail with reference to the accompanying drawings. In the description and drawings, elements having substantially the same function are designated by the same reference numerals, and repeated explanations thereof will not be provided.

1. Configuration of Material for Organic Electroluminescent Device

According to one or more embodiments of the present disclosure, the material for an organic electroluminescent device is capable of improving the emission life of the organic electroluminescent device. For example, the emission life of the organic electroluminescent device may be improved by using the material for an organic electroluminescent device as a hole transport material. Hereinafter, the configuration of the material for an organic electroluminescent device according to embodiments of the present disclosure will be explained. The material for an organic electroluminescent device according to embodiments of the present disclosure may include at least one monoamine compound represented by any one of the following Formulae I to III:

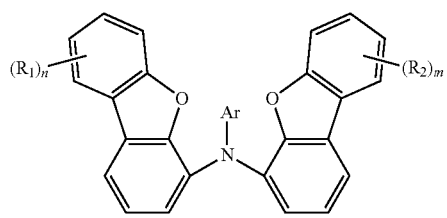

I

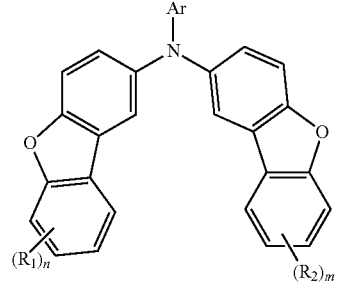

II

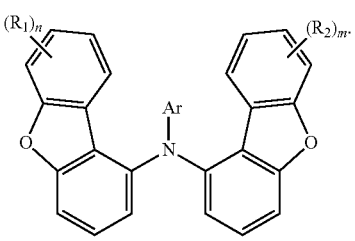

III

As used herein, an "amine" may refer to a group including a nitrogen atom and substituents combined (e.g., coupled) with the nitrogen atom, the substituents having independent from each other structures (for example, the substituents may not be combined with each other). For example, in embodiments of the present disclosure, the "amine" does not include a compound in which the substituents of the nitrogen atom having a valence of at least two are fused to each other to form a ring (for example, a compound in which nitrogen is included as one of the ring-forming atoms of a heterocyclic compound such as pyridine, carbazole, or the like). Thus, Ar may include a pyridinyl group, a carbazolyl group, and/or the like.

In Formulae I to III, Ar may be a substituted or unsubstituted aryl group having 6 to 50 carbon atoms.

For example, Ar may be selected from a substituted or unsubstituted phenyl group, a substituted or unsubstituted naphthyl group, a substituted or unsubstituted anthracenyl group, a substituted or unsubstituted phenanthrenyl group, a substituted or unsubstituted perylenyl group, a substituted or unsubstituted tetracenyl group, a substituted or unsubstituted biphenyl group, a substituted or unsubstituted terphenyl group, a substituted or unsubstituted naphthylphenyl group, a substituted or unsubstituted biphenylenyl group, a substituted or unsubstituted indenyl group, and a substituted or unsubstituted fluoranthenyl group. In some embodiments, Ar may be a group having three benzene rings, for example, the substituted or unsubstituted phenanthrenyl group, the substituted or unsubstituted terphenyl group, the substituted or unsubstituted naphthylphenyl group, and/or the like.

The substituent of the aryl group included in, for example, Ar in any of Formulae I to III may be selected from an alkyl group (for example, a methyl group, an ethyl group, and/or the like), an alkenyl group (for example, a vinyl group, an allyl group, and/or the like), a halogen atom (for example, a fluorine atom, a chlorine atom, and/or the like), a silyl group (for example, a trimethylsilyl group), a cyano group, an alkoxy group (for example, a methoxy group, a butoxy group, an octoxy group, and/or the like), a nitro group, a hydroxyl group, a thiol group, and the like. In some embodiments, the substituent may be a functional group other than a vinyl group, an indolyl group or a triphenylenyl group, to facilitate thermal stability. The substituent may also be substituted with the same functional group as the substituent.

In some embodiments, Ar may include the phenanthrenyl group. In this case, a glass transition temperature may increase for the molecular weight of the monoamine compound. Therefore, the thermal stability of the molecule itself may increase, and layer quality (e.g., quality of the hole transport layer) may be improved. Thus, when Ar in any of Formulae I to III includes the phenanthrenyl group, the emission life of the organic electroluminescent device may be markedly improved. The phenanthrenyl group may form an aromatic ring together with other atoms (for example, a hetero atom such as a nitrogen atom). In addition, in the case that Ar includes an aromatic ring having more ring-forming carbon atoms than those of the phenanthrenyl group, the energy gap of the monoamine compound may decrease, and emission efficiency may be deteriorated.

Since the monoamine compound according to embodiments of the present disclosure includes two dibenzofuran groups combined (e.g., coupled) with the nitrogen atom at the same substitution positions of the dibenzofuran groups, molecular structure of the monoamine compound is highly symmetric. Due to these structural characteristics, the emission life of the organic electroluminescent device may increase.

$R_1$ and $R_2$ in Formulae I to III may each independently be selected from a hydrogen atom, a halogen atom (for example, a fluorine atom, a chlorine atom, and/or the like), an alkyl group having 1 to 15 carbon atoms, a substituted or unsubstituted aryl group having 6 to 30 carbon atoms for forming a ring, and a substituted or unsubstituted heteroaryl group having 1 to 30 carbon atoms for forming a ring. As used herein, the statement "atoms for forming a ring" may refer to "ring-forming atoms."

The alkyl group having 1 to 15 carbon atoms may be a group having a linear shape (for example, a methyl group, an ethyl group, a propyl group, a butyl group, an octyl group, a decyl group, a pentadecyl group, and/or the like) or a branched shape (for example, a t-butyl group, and/or the like).

Non-limiting examples of the aryl group having 6 to 30 carbon atoms for forming a ring may include those illustrated above. Non-limiting examples of the heteroaryl group having 1 to 30 carbon atoms for forming a ring may include a furanyl group, a benzofuranyl group, an isobenzofuranyl group, an indazolyl group, a benzoimidazolyl group, a benzoxazolyl group, a benzotriazolyl group, a phenoxazinyl group, a tetraphenyl group, a benzoquinolinyl group, a pyrenyl group, a glyceryl group, a thiazolyl group, an isothiazolyl group, a benzothiazolyl group, a thiophenyl group, a thienothiophenyl group, a benzothiophenyl group, a dibenzothiophenyl group, a N-arylcarbazolyl group, a N-heteroarylcarbazolyl group, a N-alkylcarbazolyl group, a phenothiazyl group, a pyrimidyl group, a triazinyl group, a quinolinyl group, a quinoxalyl group, a pyridinyl group, a pyrrolyl group, a pyridazinyl group, a pyrazyl group, a pyranyl group, a quinolyl group, an isoquinolyl group, an indolyl group, a pyrazolyl group, a tetrazolyl group, an imidazolyl group, an oxazolyl group and an isoxazolyl group.

Non-limiting examples of the substituents of the aryl group and the heteroaryl group included in, for example, $R_1$ and $R_2$ in any of Formulae I to III may be the same as the examples of substituents provided in connection with the aryl group included in Ar.

n and m may each independently be an integer selected from 1 to 4. When n and/or m are equal to or greater than 2, a plurality of $R_1$(s) and/or $R_2$(s) may respectively be the same as or different from each other.

The material for an organic electroluminescent device according to embodiments of the present disclosure may be included in at least one selected from a hole transport layer and an emission layer of the organic electroluminescent device. For example, the material for an organic electroluminescent device may be included in the hole transport layer.

The organic electroluminescent device using the material for an organic electroluminescent device having the above-described configuration may have markedly improved emission life. The material for an organic electroluminescent device according to embodiments of the present disclosure may be represented by at least one of the following compounds:

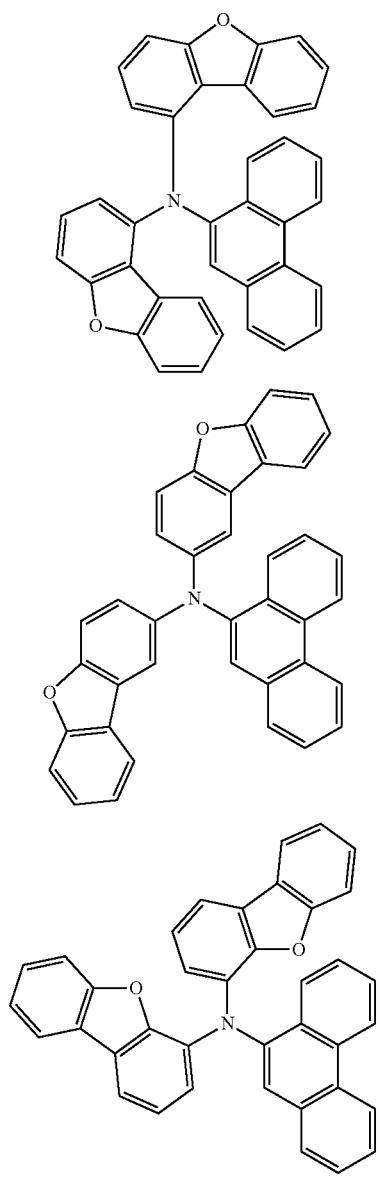

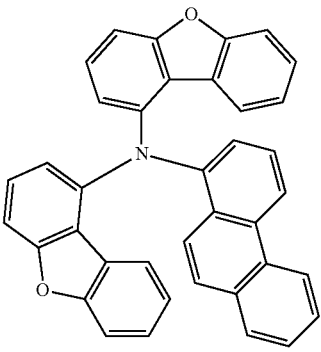
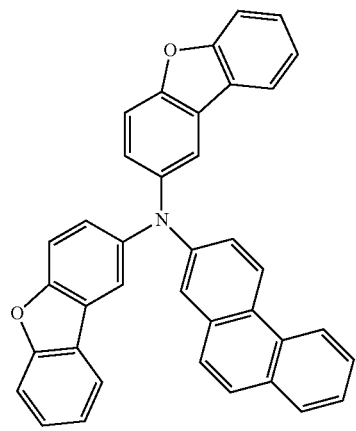
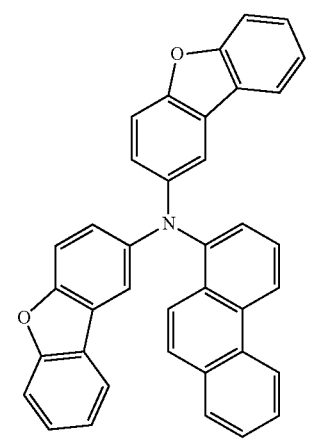
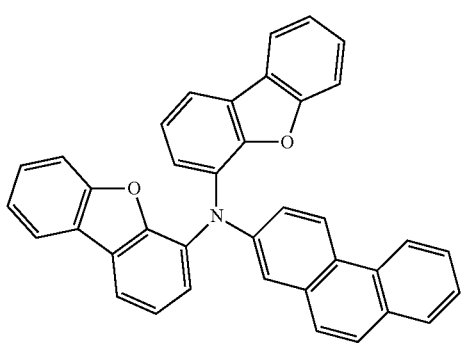
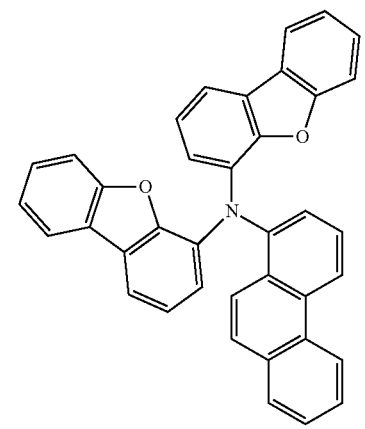 [SMILES: c1ccc2c(c1)ccc1c(N(c3cccc4c3oc3ccccc34)c3cccc4c3oc3ccccc34)cccc12]
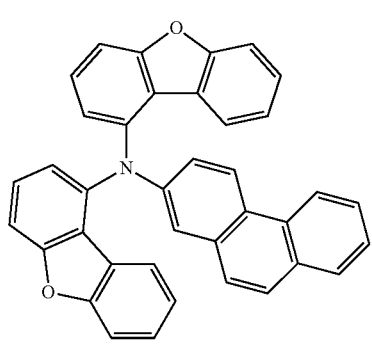
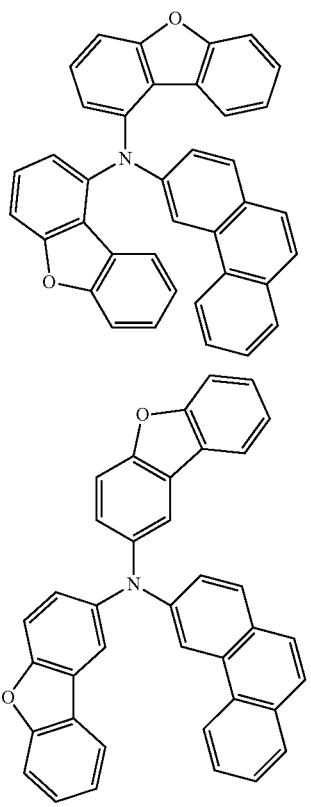

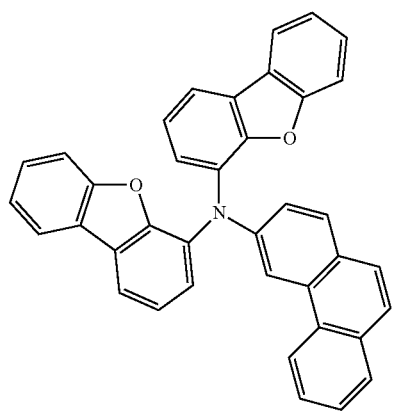
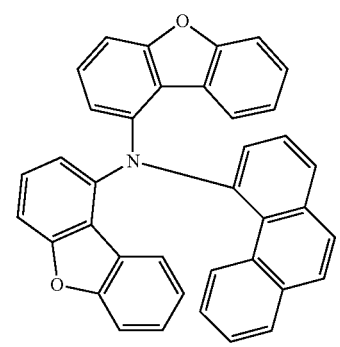
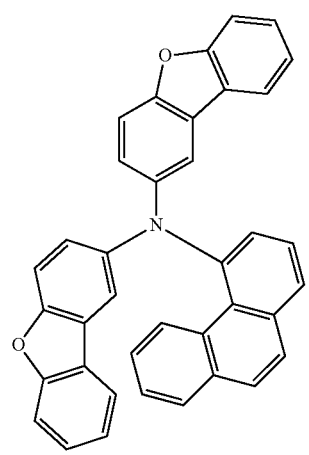
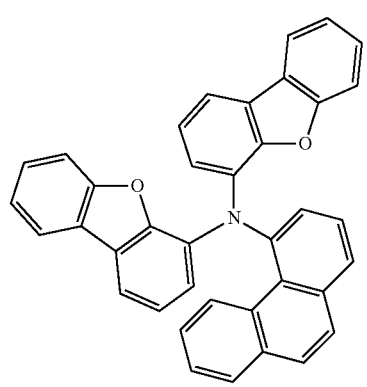
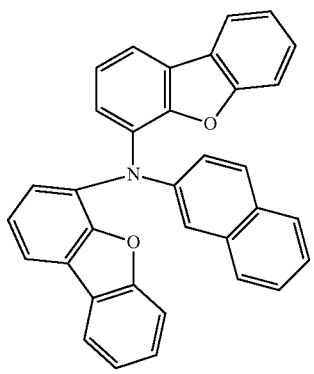
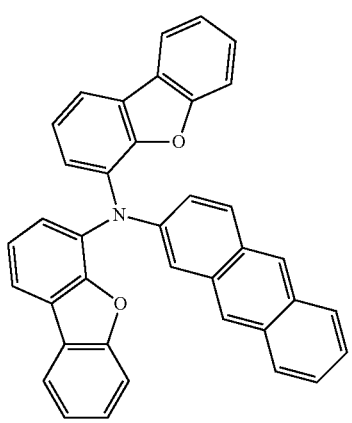
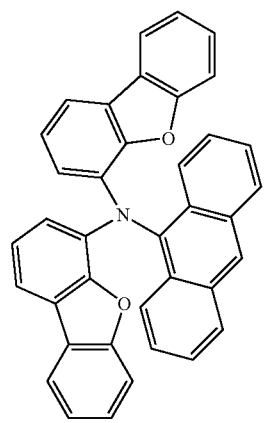
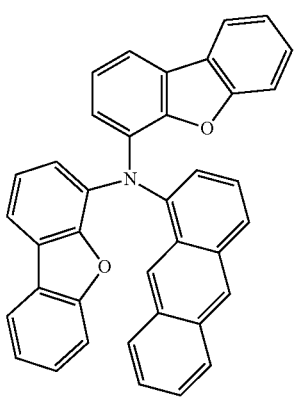

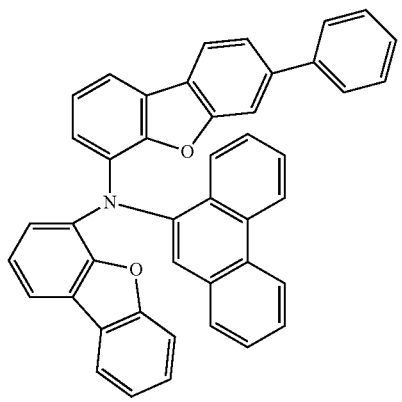
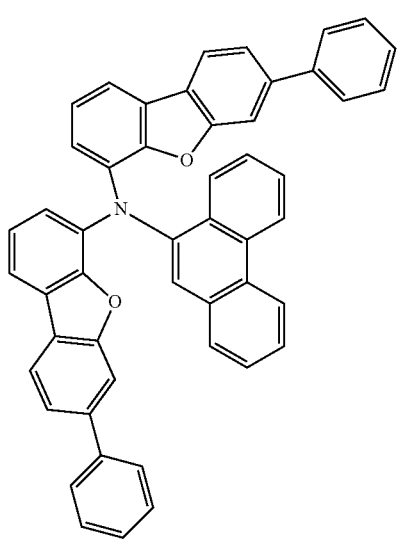
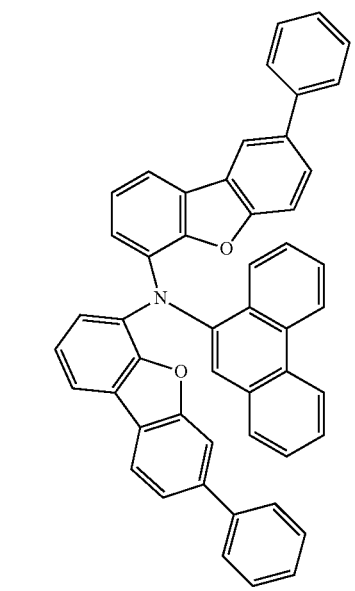
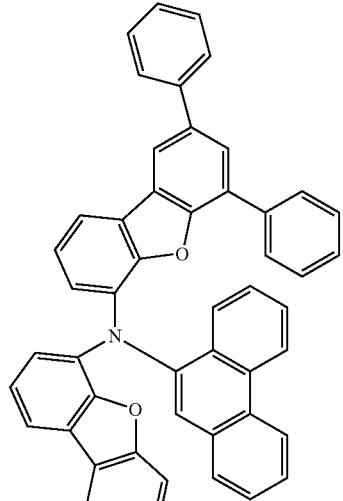
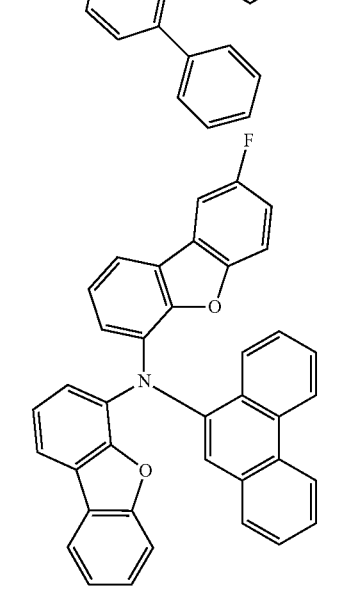
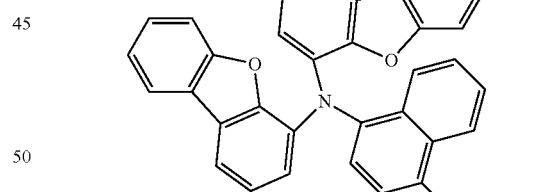
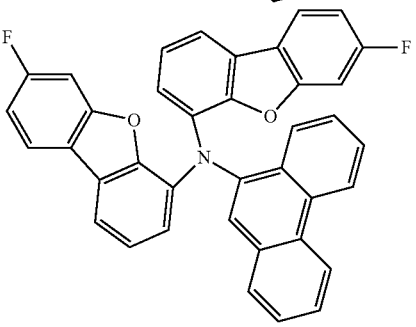

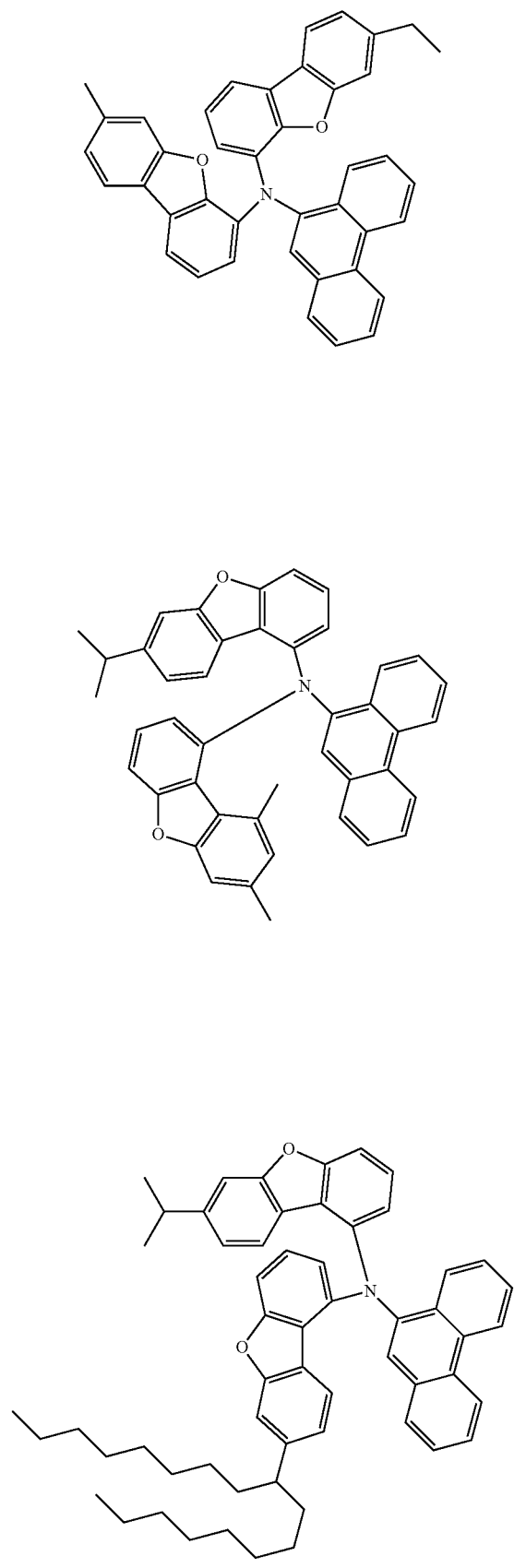
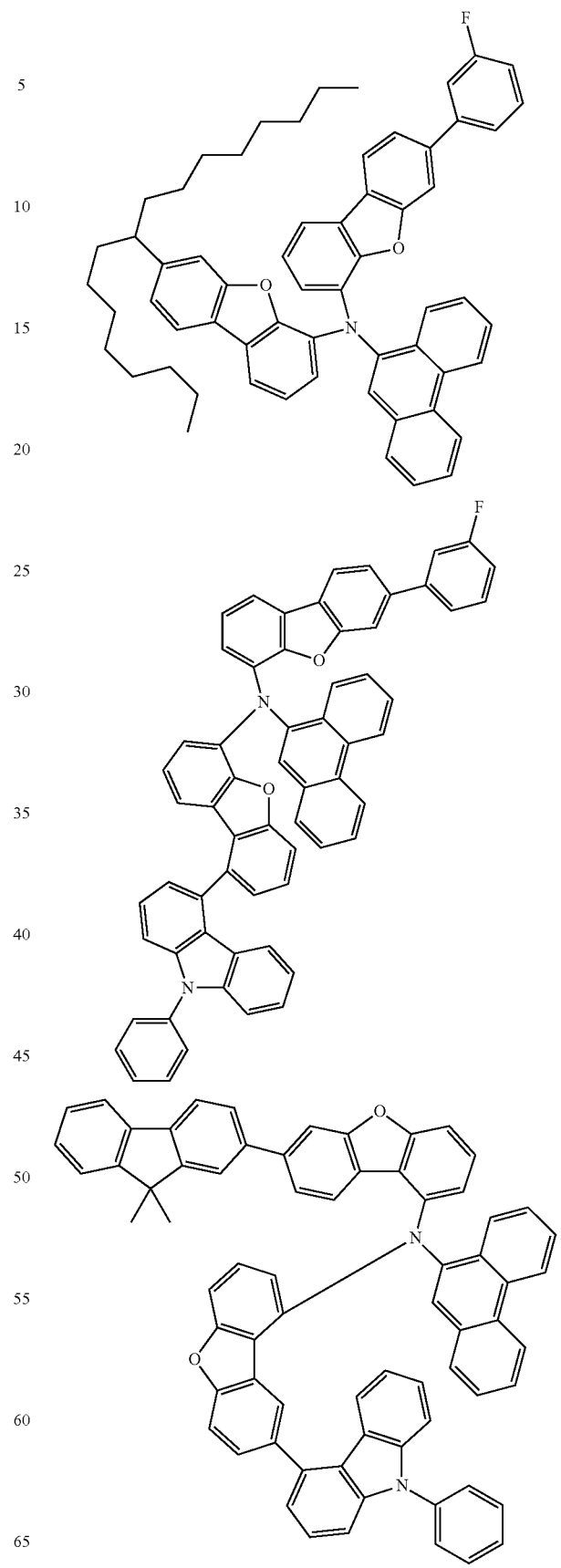

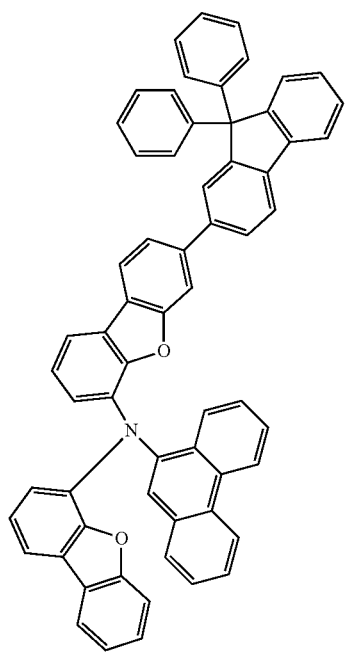 [SMILES: c1ccc(C2(c3ccccc3)c3ccccc3-c3ccc(-c4ccc5c(c4)oc4c(N(c6cc7ccccc7c7ccccc67)c6cccc7c6oc6ccccc67)cccc45)cc32)cc1]
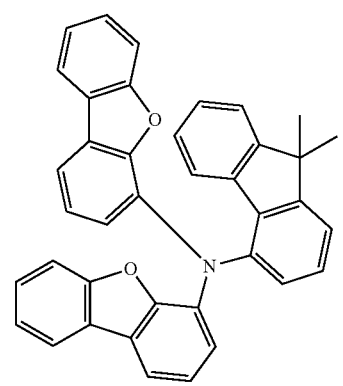
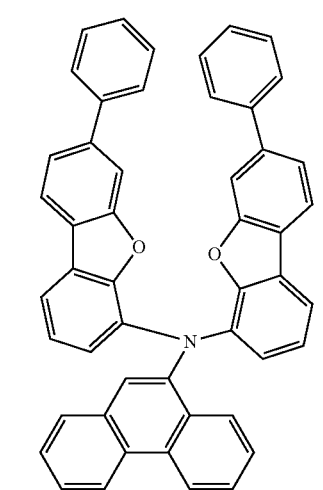
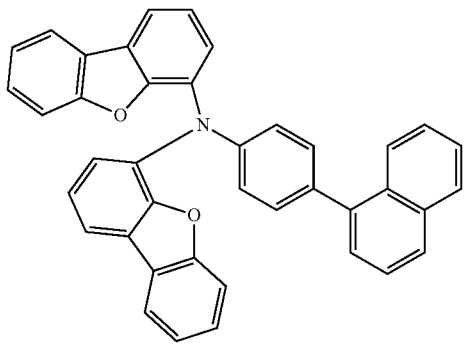
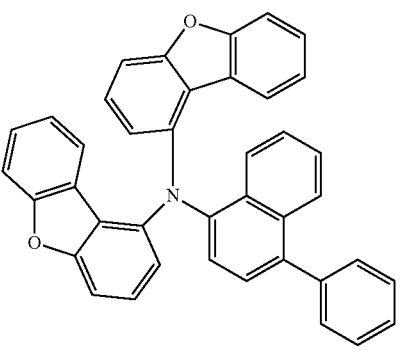
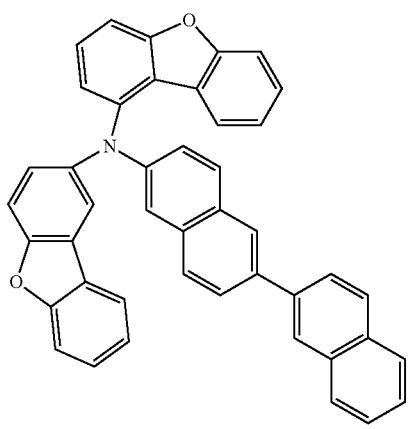
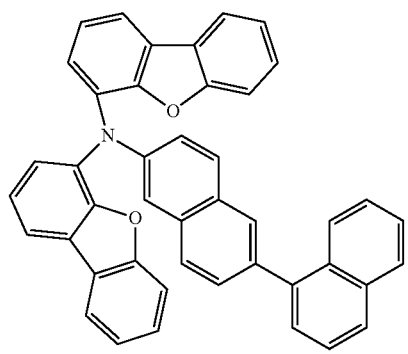

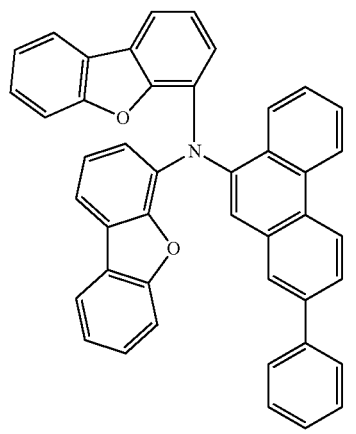
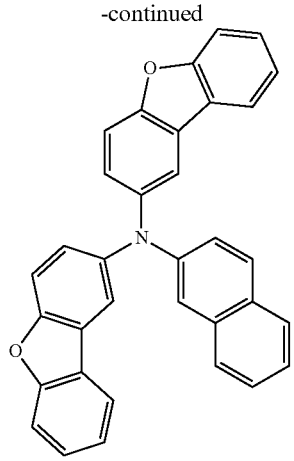
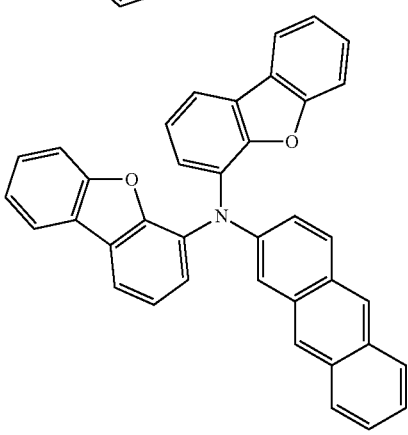
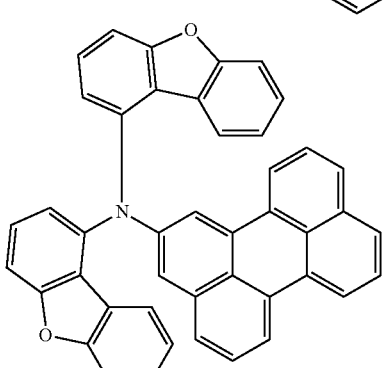
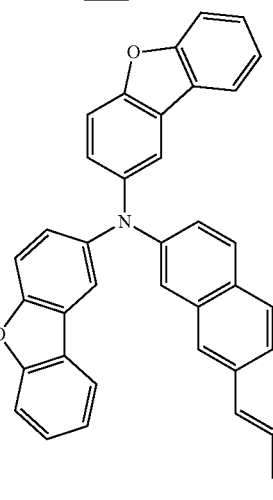

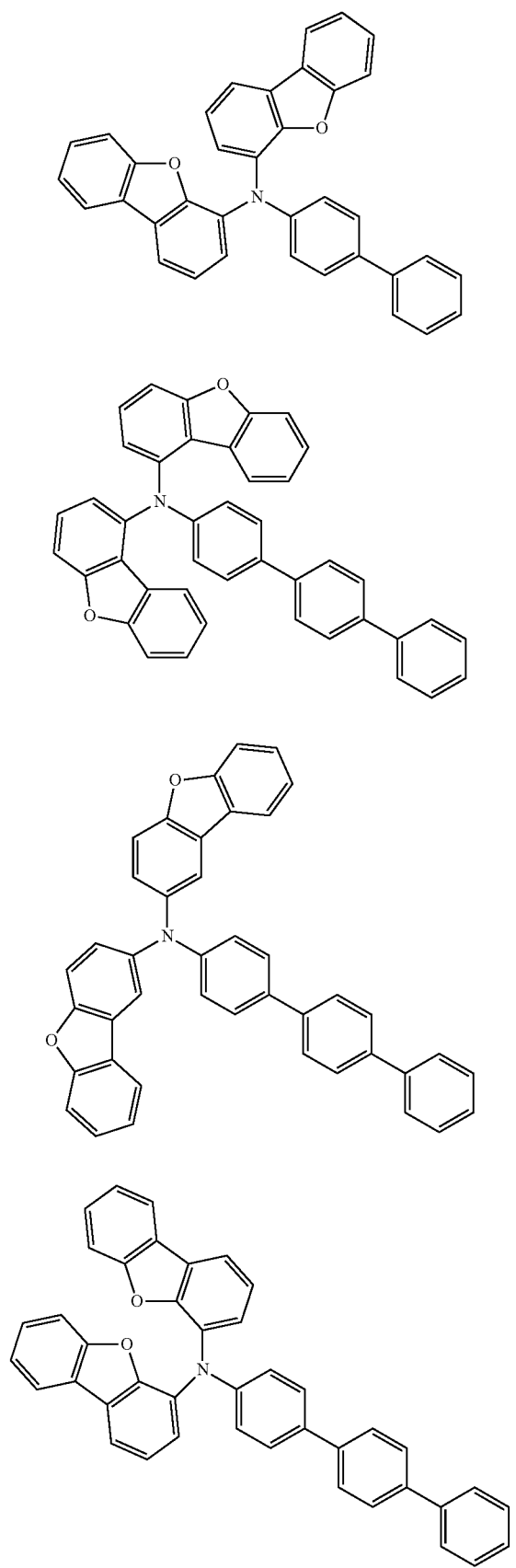
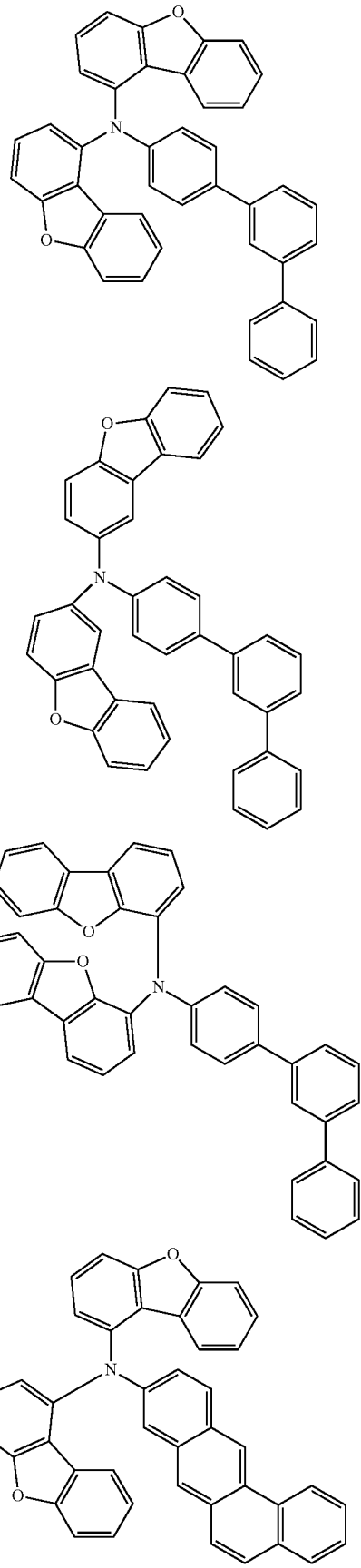

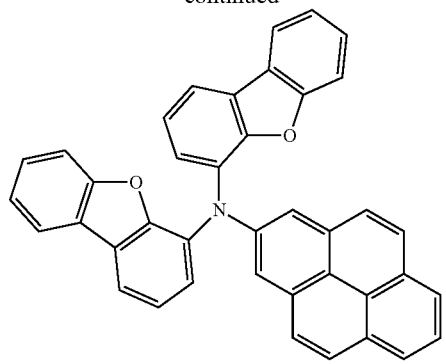
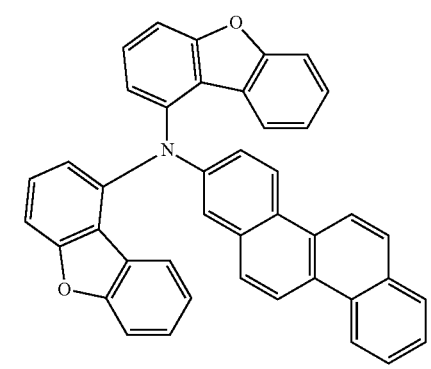
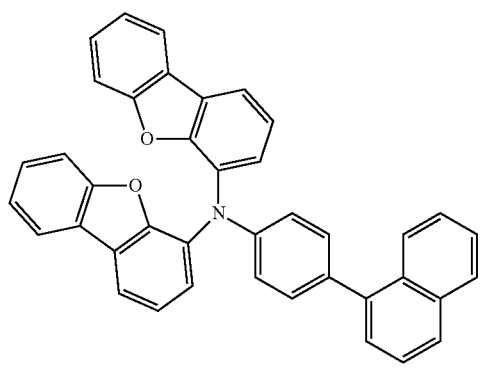
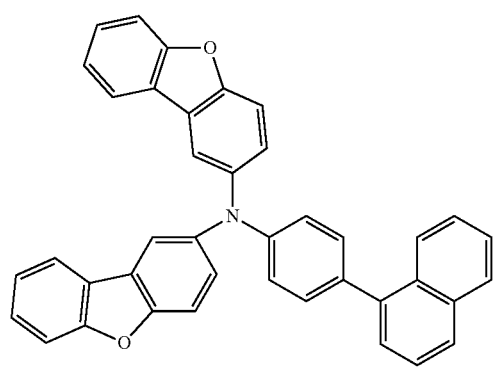
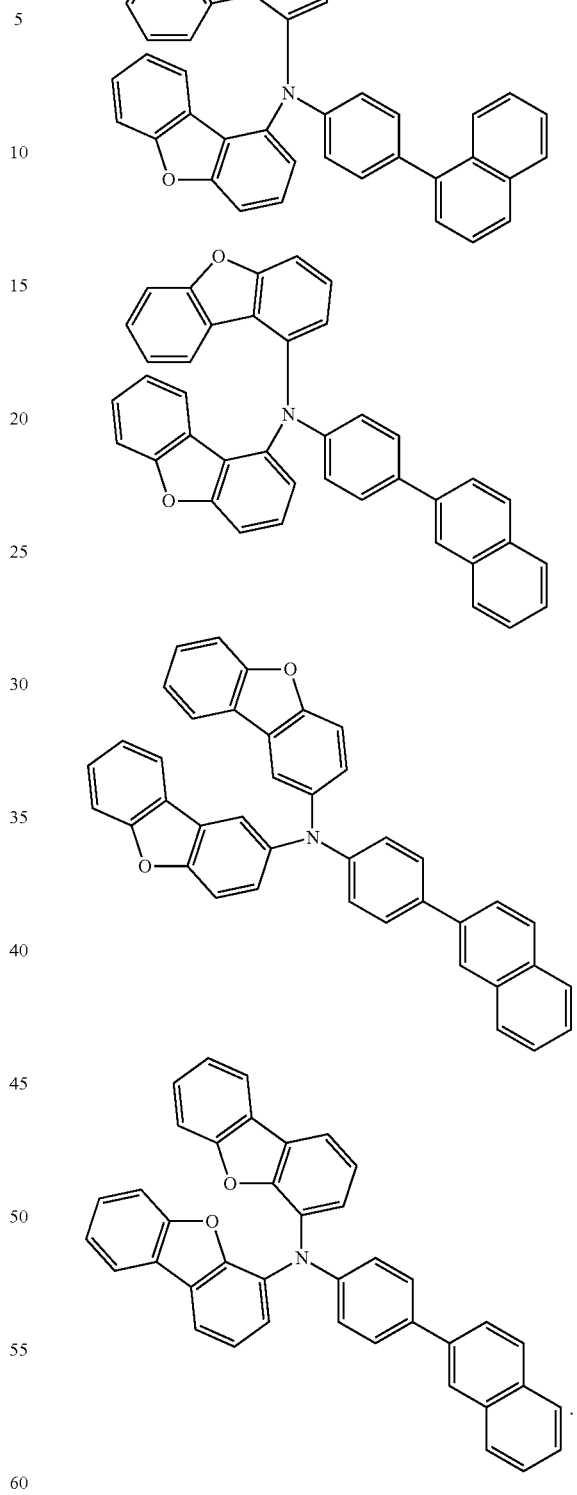
2. Configuration of Organic Electroluminescent Device Using the Material for Organic Electroluminescent Device
An organic electroluminescent device using the material for an organic electroluminescent device according to embodiments of the present disclosure will be described with reference to FIG. 1. FIG. 1 is a schematic cross-sectional view of an organic electroluminescent device according to one or more embodiments of the present disclosure.

As shown in FIG. 1, an organic electroluminescent device 100 according to embodiments of the present disclosure may include a substrate 110, a first electrode 120 positioned on the substrate 110, a hole injection layer 130 positioned on the first electrode 120, a hole transport layer 140 positioned on the hole injection layer 130, an emission layer 150 positioned on the hole transport layer 140, an electron transport layer 160 positioned on the emission layer 150, an electron injection layer 170 positioned on the electron transport layer 160 and a second electrode 180 positioned on the electron injection layer 170.

The material for an organic electroluminescent device according to embodiments of the present disclosure may be included in at least one selected from the hole transport layer 140 and the emission layer 150. For example, the material for an organic electroluminescent device may be included in both the hole transport layer 140 and the emission layer 150. In some embodiments, the material for an organic electroluminescent device may be included in the hole transport layer 140.

Each of the organic thin layers positioned between the first electrode 120 and the second electrode 180 of the organic electroluminescent device 100 may be formed by one or more suitable methods including, without limitation, an evaporation method, and/or the like.

The substrate 110 may be any suitable substrate for an organic electroluminescent device. For example, the substrate 110 may be a glass substrate, a semiconductor substrate, or a transparent plastic substrate.

The first electrode 120 may be, for example, an anode and may be formed on the substrate 110 by an evaporation method, a sputtering method, and/or the like. For example, the first electrode 120 may be formed as a transmission type (e.g., transmission kind) electrode using a metal having high work function such as an alloy, a conductive compound, and/or the like. The first electrode 120 may be formed using, for example, transparent and highly conductive indium tin oxide (ITO), indium zinc oxide (IZO), tin oxide ($SnO_2$), zinc oxide (ZnO), and/or the like. In some embodiments, the anode 120 may be formed as a reflection type (e.g., reflection kind) electrode using magnesium (Mg), aluminum (Al), and/or the like.

On the first electrode 120, the hole injection layer 130 may be formed. The hole injection layer 130 is a layer capable of facilitating the injection of holes from the first electrode 120 and the hole injection layer 130 may be formed, for example, on the first electrode 120 to a thickness from about 10 nm to about 150 nm. The hole injection layer 130 may be formed using any suitable material. Non-limiting examples of the material for forming the hole injection layer may include triphenylamine-containing poly ether ketone (TPAPEK), 4-isopropyl-4'-methyldiphenyliodoniumtetrakis(pentaflorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methyl phenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-NATA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), polyaniline/poly(4-styrenesulfonate (PANI/PSS), and the like.

On the hole injection layer 130, the hole transport layer 140 may be formed. In some embodiments, the hole transport layer 140 may be formed by stacking a plurality of layers. The hole transport layer 140 is a layer including a hole transport material capable of performing hole transporting function and may be formed, for example, on the hole injection layer 130 to a thickness from about 10 nm to about 150 nm. The hole transport layer 140 may be formed using the material for an organic electroluminescent device according to embodiments of the present disclosure. In some embodiments, the material for an organic electroluminescent device according to embodiments of the present disclosure may be used as the host material in the emission layer 150, and the hole transport layer 140 may be formed using any suitable hole transport material commonly known to those skilled in the art. For example, the hole transport material may include 1,1-bis[(di-4-tolylamino)phenyl]cyclohexane (TAPC), a carbazole derivative (such as N-phenyl carbazole, polyvinyl carbazole, and/or the like), N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), and/or the like.

On the hole transport layer 140, the emission layer 150 may be formed. The emission layer 150 may be formed to a thickness from about 10 nm to about 60 nm. The material for forming the emission layer 150 may be any suitable luminescent material, without specific limitation, and may be selected from fluoranthene derivatives, pyrene derivatives, arylacetylene derivatives, fluorene derivatives, perylene derivatives, chrysene derivatives, and the like. In some embodiments, the pyrene derivatives, the perylene derivatives and the anthracene derivatives may be used. For example, as the material for the emission layer 150, an anthracene derivative represented by the following Formula 3 may be used:

Formula 3

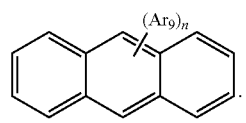

(3)

In the above Formula 3, $Ar_9$ may be selected from a hydrogen atom, a deuterium atom, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a heteroaryl group having 5 to 50 carbon atoms for forming a ring, a substituted or unsubstituted silyl group, a carboxyl group, a halogen atom, a cyano group, a nitro group and a hydroxyl group; and n may be an integer selected from 1 to 10.

For example, in Formula 3, $Ar_9$ may be selected from a phenyl group, a biphenyl group, a terphenyl group, a naphthyl group, a phenylnaphthyl group, a naphthylphenyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothienyl group, and the like. In some embodiments, the phenyl group, the biphenyl group, the terphenyl group, the fluorenyl group, the carbazolyl group, the dibenzofuranyl group, and/or the like may be included in Arg.

The compound represented by Formula 3 may be represented by at least one of Compounds a-1 to a-12. However, the compound represented by Formula 3 is not limited thereto. In Compounds a-1 to a-12, "D" may refer to deuterium.

a-1 a-2 a-3 a-4
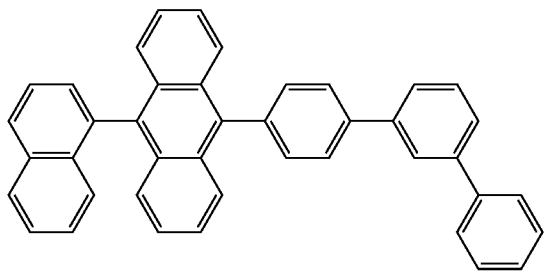

a-5 a-6
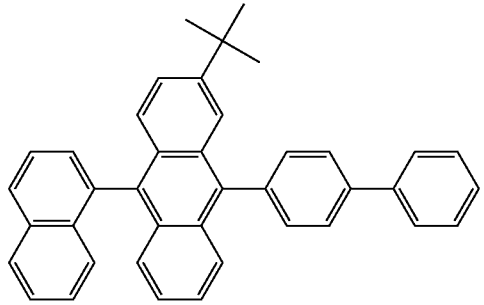

a-7
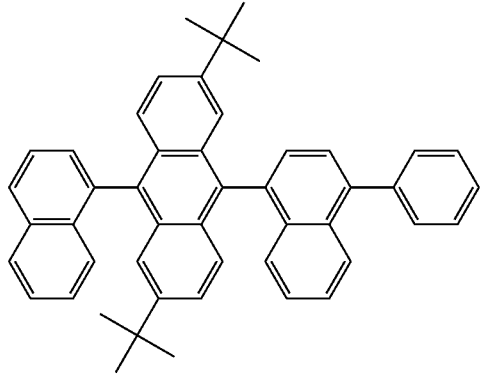

a-8
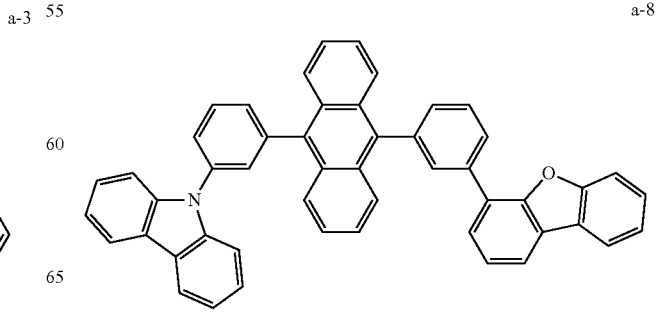

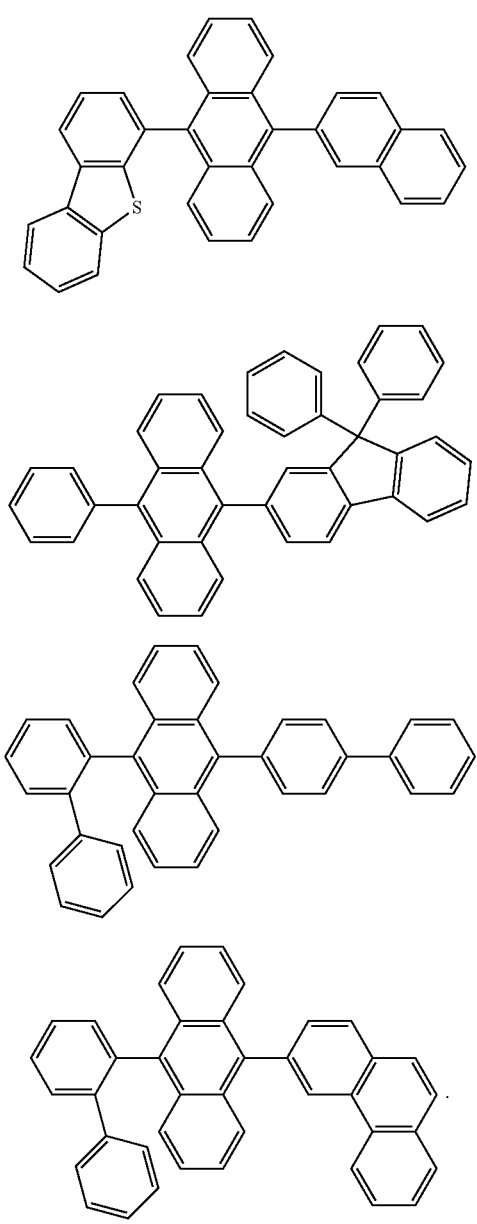

a-9 a-10 a-11 a-12

The emission layer 150 may include a dopant selected from styryl derivatives (for example, 1,4-bis[2-(3-N-ethyl-carbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl)-N-phenylbenzeneamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene), and the like, but embodiments of the present disclosure are not limited thereto.

On the emission layer 150, for example, an electron transport layer 160 may be formed. The electron transport layer 160 may include a material having tris(8-hydroxyquinolinato)aluminum (Alq3) or a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridin-3-yl) biphenyl-3-yl)-1,3,5-triazine, and/or a material including an imidazole derivative such as 2-(4-(N-phenylbenzoimidazolyl-1-ylphenyl)-9,10-dinaphthylanthracene)). The electron transport layer 160 is a layer including an electron transport material capable of performing electron transporting function, and the electron transport layer 160 may be formed on the emission layer 150 to a thickness from about 15 nm to about 50 nm. On the electron transport layer 160, the electron injection layer 170 may be formed using a material including, for example, lithium fluoride, lithium-8-quinolinato (Liq), and/or the like. The electron injection layer 170 is a layer capable of facilitating the injection of electrons from the second electrode 180, and the electron injection layer 170 may be formed to a thickness from about 0.3 nm to about 9 nm.

On the electron injection layer 170, the second electrode 180 may be formed. The second electrode 180 may be, for example, a cathode. In some embodiments, the second electrode 180 may be formed as a reflection type (e.g., reflection kind) electrode using a metal having low work function, for example, an alloy, a conductive compound, and/or the like. The second electrode 180 may be formed using, for example, lithium (Li), magnesium (Mg), aluminum (Al), aluminum-lithium (Al—Li), calcium (Ca), magnesium-indium (Mg—In), magnesium-silver (Mg—Ag), and/or the like. In some embodiments, the second electrode 180 may be formed as a transmission type (e.g., transmission kind) electrode using Indium Tin Oxide (ITO), Indium Zinc Oxide (IZO), and/or the like. Each of the above-mentioned layers may be formed by selecting one or more suitable layer forming methods such as, for example, a vacuum evaporation method, a sputtering method, various coating methods, and/or the like, depending on the materials used for forming each layer.

Hereinabove, the structure of the organic electroluminescent device 100 according to an embodiment of the present disclosure has been explained. The organic electroluminescent device 100 including the material for an organic electroluminescent device according to embodiments of the present disclosure has improved emission life.

However, the structure of the organic electroluminescent device 100 is not limited to the above-described embodiments and may include structures of various other suitable organic electroluminescent devices. For example, the organic electroluminescent device 100 may be provided without one or more layers selected from the hole injection layer 130, the electron transport layer 160 and the electron injection layer 170. In some embodiments, the layers of the organic electroluminescent device 100 may each independently be formed as a single layer or a multilayer.

In some embodiments, the organic electroluminescent device 100 may be provided with a hole blocking layer between the electron transport layer 160 and the emission layer 150 to prevent or reduce the diffusion of triplet excitons or holes into the electron transport layer 160. The hole blocking layer may be formed using, for example, oxadiazole derivatives, triazole derivatives and/or phenanthroline derivatives.

EXAMPLES

Hereinafter, the organic electroluminescent device according to embodiments of the present disclosure will be explained in more detail by referring to examples and comparative examples. However, the following examples are only illustrations of the organic electroluminescent device according to the present disclosure, and the organic electroluminescent device according to the present disclosure is not limited thereto.

Synthetic Example 1

Synthesis of Compound C

Compound C (an example of the monoamine represented by Formula III) was synthesized according to the following synthetic scheme:

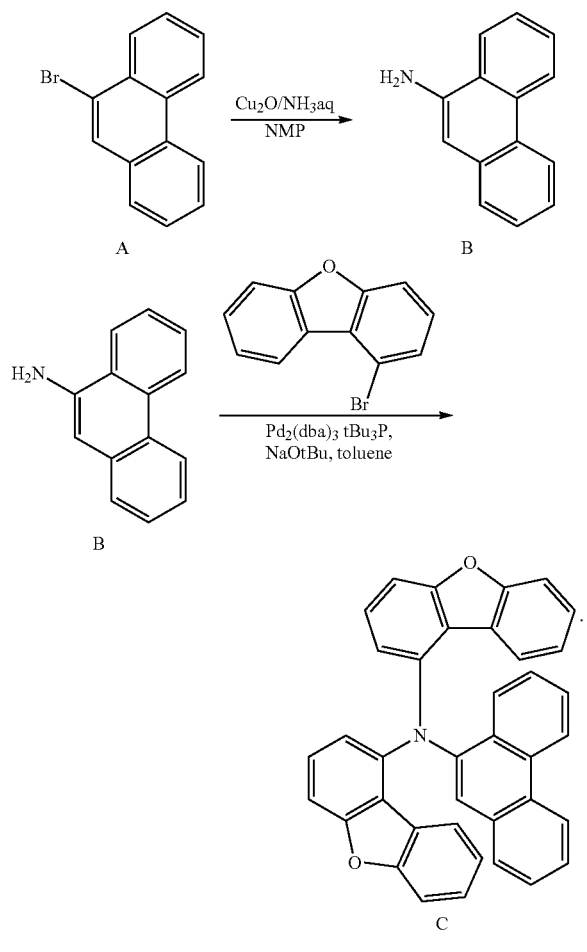

Synthesis of Compound B

Under an argon atmosphere, 15.00 g of Compound A, 0.85 g of cuprous oxide, 20 ml of an aqueous ammonia solution and 70 ml of NMP were added to a 500 ml, three necked flask, followed by heating at about 110° C. for about 25 hours. After air cooling the resultant, water was added thereto, an organic layer was separated therefrom, and solvents were distilled. The crude product thus obtained was separated using silica gel column chromatography (using hexane/ethyl acetate) to produce 7.4 g of Compound B as a white solid (Yield 66%). The molecular weight of Compound B thus obtained was measured using Fast Atom Bombardment Mass Spectrometry (FAB-MS), and a value of 193 ($C_{14}H_{11}N$) was obtained.

Synthesis of Compound C

Under an argon atmosphere, 1.00 g of Compound B, 2.81 g of 1-bromodibenzofuran, 0.27 g of bis(dibenzylideneacetone)palladium(0), 0.088 g of tri-tert-butylphosphine and 3.98 g of sodium tert-butoxide were added to a 500 ml, three necked flask, followed by heating and refluxing in 200 ml of a toluene solvent for about 7 hours. After air cooling the resulting reactant, water was added to the reactant, an organic layer was separated therefrom, and solvents were distilled. The crude product thus obtained was separated using silica gel column chromatography (using toluene/hexane) to produce 1.90 g of Compound C as a white solid (Yield 70%). The molecular weight of Compound C thus obtained was measured using FAB-MS, and a value of 525 ($C_{38}H_{23}NO_2$) was obtained. In addition, the glass transition temperature of Compound C was measured using a differential scanning calorimetry (DSC 7020 of Hitachi Hightech Co.) and a value of 120° C. was obtained.

Synthetic Example 2

Synthesis of Compound D

Compound D (an example of the monoamine represented by Formula II) was synthesized according to the following synthetic scheme:

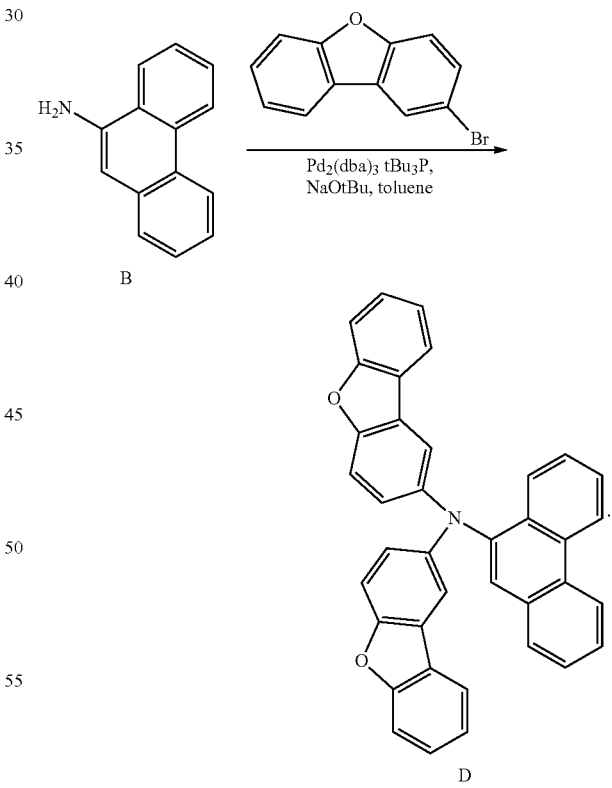

Figure 2:
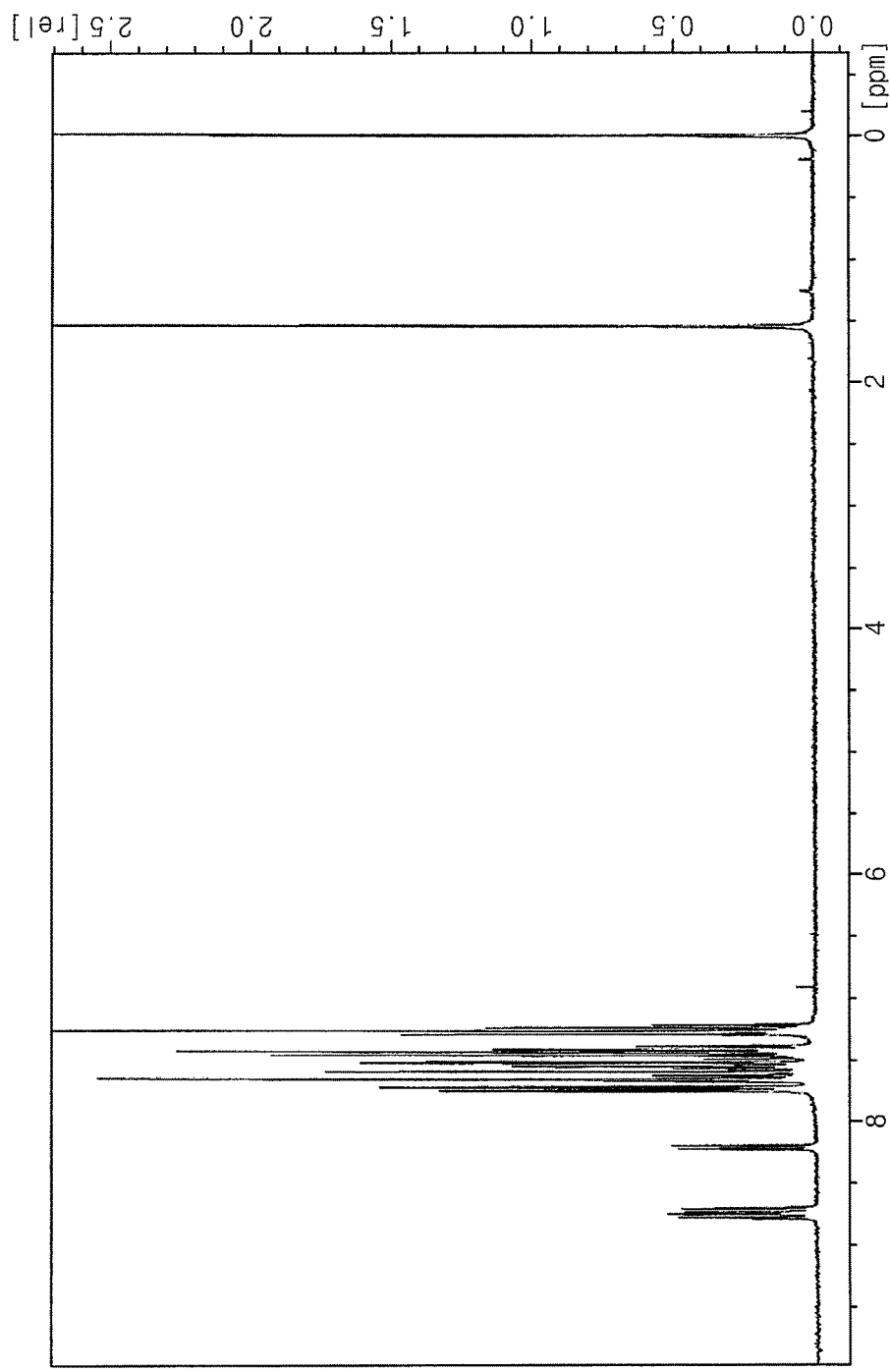
FIG. 2 illustrates an NMR spectrum of Compound D.

Under an argon atmosphere, 1.00 g of Compound B, 2.82 g of 2-bromodibenzofuran, 0.27 g of bis(dibenzylideneacetone)palladium(0), 0.088 g of tri-tert-butylphosphine and 3.98 g of sodium tert-butoxide were added to a 500 ml, three necked flask, followed by heating and refluxing in 200 ml of a toluene solvent for about 7 hours. After air cooling the resulting reactant, water was added to the reactant, an organic layer was separated therefrom, and solvents were distilled. The crude product thus obtained was separated using silica gel column chromatography (using toluene/hexane) to produce 1.85 g of Compound D as a white solid (Yield 68%). The molecular weight of Compound D thus obtained was measured using FAB-MS, and a value of 525 ($C_{38}H_{23}NO_2$) was obtained. In addition, $^1$H NMR ($CDCl_3$, 300 MHz) of Compound D was measured, and NMR spectrum shown in FIG. 2 was obtained. Thus, the synthesized compound was confirmed to be Compound D. In addition, the glass transition temperature of Compound D was measured using a differential scanning calorimetry (DSC 7020 of Hitachi Hightech Co.) and a value of 115° C. was obtained.

Synthetic Example 3

Synthesis of Compound E

Compound E (an example of the monoamine represented by Formula I) was synthesized according to the following synthetic scheme:

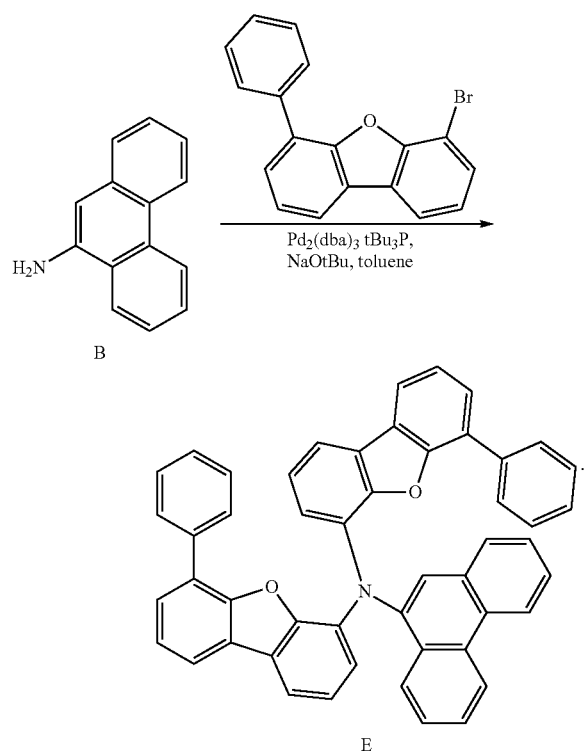

Under an argon atmosphere, 1.00 g of Compound B, 3.68 g of 4-bromo-6-phenyldibenzofuran, 0.27 g of bis(dibenzylideneacetone)palladium(0), 0.088 g of tri-tert-butylphosphine and 3.98 g of sodium tert-butoxide were added to a 500 ml, three necked flask, followed by heating and refluxing in 200 ml of a toluene solvent for about 7 hours. After air cooling the resulting reactant, water was added to the reactant, an organic layer was separated therefrom, and solvents were distilled. The crude product thus obtained was separated using silica gel column chromatography (using toluene and hexane) to produce 2.38 g of Compound E as a white solid (Yield 68%). The molecular weight of Compound E thus obtained was measured using FAB-MS, and a value of 677 ($C_{50}H_{31}NO_2$) was obtained. In addition, $^1$H NMR ($CDCl_3$, 300 MHz) of Compound E was measured, and NMR spectrum similar to that of Compound D was obtained. Thus, the synthesized compound was confirmed to be Compound E. In addition, the glass transition temperature of Compound E was measured using a differential scanning calorimetry (DSC 7020 of Hitachi Hightech Co.) and a value of 118° C. was obtained.

(Evaluation of Glass Transition Temperature)

The following Compound C3 was prepared as a comparative example. Compound C3 is commonly known to those skilled in the art of organic electroluminescent devices. The glass transition temperature of Compound C3 was measured using a differential scanning calorimetry (DSC 7020 of Hitachi Hightech Co.) and a value of 100° C. was obtained. When comparing the glass transition temperature of Compounds C, D and E with that of Compound C3, the glass transition temperature of Compounds C, D and E was significantly higher than that of Compound C3, even though the molecular weights of the compounds (Compounds C, D, E and C3) are similar. Without being bound by any particular theory, it is believed that the glass transition temperature was increased by including a phenanthrenyl group as Ar in Formulae I to III. Thus, the thermal stability of the organic electroluminescent device including one of Compounds C, D and E in the hole transport layer or the emission layer may be improved.

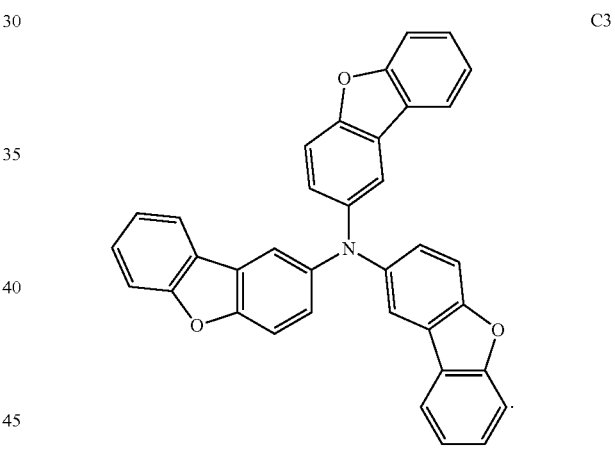

(Manufacture of Organic Electroluminescent Device)

An organic electroluminescent device was manufactured by the following method. First, on an ITO-glass substrate patterned and washed in advance, surface treatment using UV-ozone ($O_3$) was conducted. The layer thickness of the resulting ITO layer (as the first electrode) was about 150 nm. After ozone treatment, the substrate was washed. After finishing washing, the substrate was set in a glass bell jar type evaporator (e.g., a glass bell bar evaporator) for forming organic layers, and a hole injection layer, a HTL (a hole transport layer), an emission layer and an electron transport layer were evaporated one by one in a vacuum degree of about $10^{-4}$ to about $10^{-5}$ Pa. The material for the hole injection layer was 2-TNATA, and the thickness thereof was about 60 nm. The respective materials for the HTL are shown in Table 1, and the thickness thereof was about 30 nm.

In addition, the thickness of the emission layer was about 25 nm. The host material in the emission layer was 9,10-di(2-naphthyl)anthracene (ADN). A dopant was 2,5,8,11-tetrat-butylperylene (TBP). The doped amount of the dopant was about 3 wt % on the basis of the amount of the host. The material for the electron transport layer was Alq3, and the thickness thereof was about 25 nm. Subsequently, the substrate was transferred to a glass bell jar type evaporator for forming a metal layer, and the electron injection layer and a cathode material were evaporated in a vacuum degree of about $10^{-4}$ to about $10^{-5}$ Pa. The material for the electron injection layer was LiF, and the thickness thereof was about 1.0 nm. The material of the second electrode (cathode) was Al, and the thickness thereof was about 100 nm.

TABLE 1

| Example of device manufacture | HTL | Current density (mA/cm$^2$) | Voltage (V) | Emission efficiency (cd/A) | Half Life LT50 (hr) |
| --- | --- | --- | --- | --- | --- |
| Example 1 | Example Compound C | 10 | 6.3 | 7.2 | 2,000 |
| Example 2 | Example Compound D | 10 | 6.3 | 7.0 | 1,900 |
| Example 3 | Example Compound E | 10 | 6.3 | 7.0 | 1,700 |
| Comparative Example 1 | Comparative Compound C1 | 10 | 6.6 | 7.0 | 1,400 |
| Comparative Example 2 | Comparative Compound C2 | 10 | 6.6 | 7.0 | 1,500 |
| Comparative Example 3 | Comparative Compound C3 | 10 | 6.6 | 7.0 | 1,350 |

In Table 1, Comparative Compounds C1 and C2 are represented by the formulae illustrated below. Compounds C1 and C2 are examples of the compounds in which combination positions (e.g., coupling positions) of dibenzofuran groups to nitrogen are not symmetric (the same). Compounds C1 and C2 may be synthesized via the reaction of Compound B with bromodibenzofuran having respectively different coupling position of bromine.

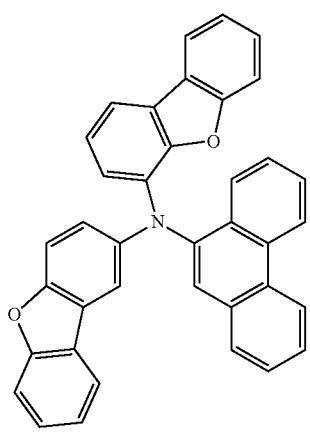

C1

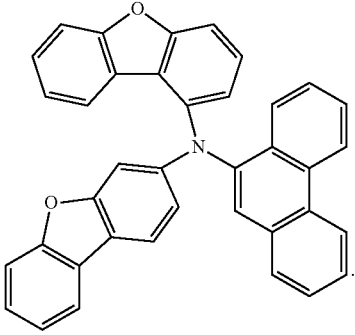

C2

(Evaluation of Properties)

The driving voltage and the emission life of each of the organic electroluminescent devices thus manufactured were measured. The electroluminescent properties were evaluated using C9920-11 brightness light distribution characteristics measurement system of HAMAMATSU Photonics Co. In addition, current density was measured at 10 mA/cm$^2$, and half life was measured at 1,000 cd/m$^2$. The results are shown in Table 1.

According to the results shown in Table 1, the life of organic electroluminescent devices of Examples 1 to 3 was improved when compared to that of organic electroluminescent devices of Comparative Examples 1 to 3. When comparing organic electroluminescent devices of Examples 1 to 3 with that of Comparative Example 3, the glass transition temperature of Compounds C, D and E respectively used in the organic electroluminescent devices of Examples 1, 2, and 3 was higher than that of Compound C3 used in the organic electroluminescent device of Comparative Example 3, and so, the thermal stability of a molecule itself and layer quality were improved for the organic electroluminescent devices of Examples 1, 2, and 3 using Compounds C, D and E, respectively. It is believed that as a result, cycle life of the organic electroluminescent devices of Examples 1 to 3 was increased as compared to that of the organic electroluminescent device of Comparative Example 3. When comparing organic electroluminescent devices of Examples 1 to 3 with those of Comparative Examples 1 and 2, Compounds C1 and C2 (respectively used in Comparative Examples 1 and 2) are supposed to have a similar glass transition temperature as that of Compound C, D and E (respectively used in Examples 1, 2, and 3). However, the life of the organic electroluminescent devices of Examples 1 to 3 was improved as compared to that of the organic electroluminescent devices of Comparative Examples 1 and 2. It is believed that these results are at least in part due to the high molecular symmetric properties of Compound C, D and E.

In example embodiments, the emission life of the organic electroluminescent device was significantly improved, especially in a blue region. In addition, since the compound group of the material for an organic electroluminescent device according to example embodiments of the present disclosure has a wide energy gap which may correspond to a blue region, application in a region from green to red (e.g., in red and green emission regions) may be possible.

As described above, since the material for an organic electroluminescent device according to example embodiments of the present disclosure includes a monoamine compound represented by one of Formulae I to III, the emission life of the organic electroluminescent device using the material may be significantly improved. Thus, the material for an organic electroluminescent device according to example embodiments of the present disclosure may have various practical applications.

As described above, the emission life of the organic electroluminescent device according to embodiments of the present disclosure may be improved.

As used herein, the term "and/or" includes any and all combinations of one or more of the associated listed items. Expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

As used herein, the terms "substantially," "about," and similar terms are used as terms of approximation and not as terms of degree, and are intended to account for the inherent deviations in measured or calculated values that would be recognized by those of ordinary skill in the art.

As used herein, the statement "atoms for forming a ring" may refer to "ring-forming atoms."

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

It will be understood that the above-disclosed embodiments are to be considered illustrative and not restrictive, and the appended claims and equivalents thereof are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing description.

What is claimed is:

1. A material for an organic electroluminescent device, the material comprising at least one monoamine compound represented by Formula I:

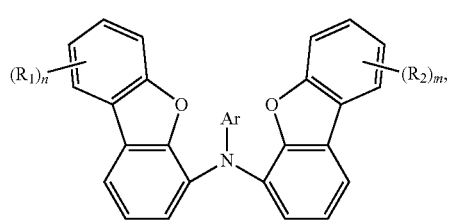

wherein in Formula I,

Ar is selected from a substituted or unsubstituted naphthyl group, a substituted or unsubstituted anthracenyl group, a substituted or unsubstituted phenanthrenyl group, a substituted or unsubstituted perylenyl group, a substituted or unsubstituted tetracenyl group, a substituted or unsubstituted naphthylphenyl group, a substituted or unsubstituted biphenylenyl group, a substituted or unsubstituted indenyl group, and a substituted or unsubstituted fluoranthenyl group, $R_1$ and $R_2$ are each independently selected from a hydrogen atom, a halogen atom, an alkyl group having 1 to 15 carbon atoms, a substituted or unsubstituted aryl group having 6 to 30 carbon atoms for forming a ring, and a substituted or unsubstituted heteroaryl group having 1 to 30 carbon atoms for forming a ring, n and m are each independently an integer selected from 1 to 4, wherein a direct substituent of the substituted Ar is selected from the group consisting of an alkyl group, an alkenyl group, a halogen atom, a silyl group, a cyano group, an alkoxy group, a nitro group, a hydroxyl group, a phenyl group, a naphthyl group, a biphenyl group, and a thiol group.

2. The material of claim 1, wherein Ar is selected from a substituted or unsubstituted phenanthrenyl group and a substituted or unsubstituted naphthylphenyl group.

3. The material of claim 2, wherein Ar comprises the substituted or unsubstituted phenanthrenyl group.

4. The material of claim 1, wherein the monoamine compound is represented by at least one of the following compounds:

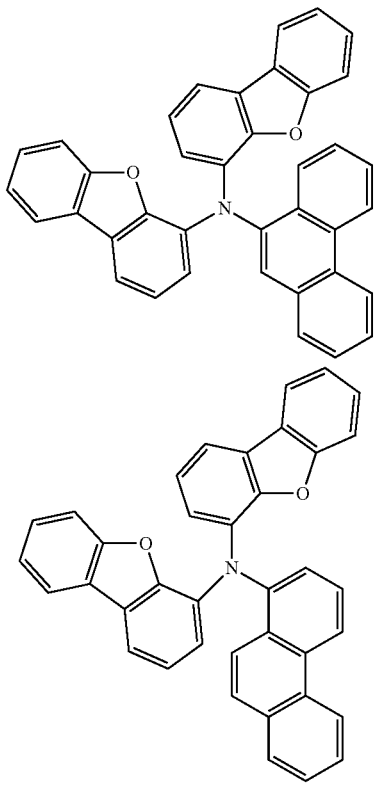

37
-continued
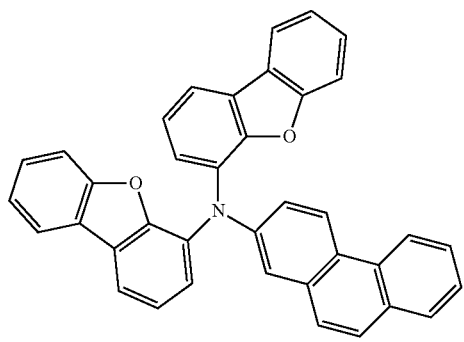
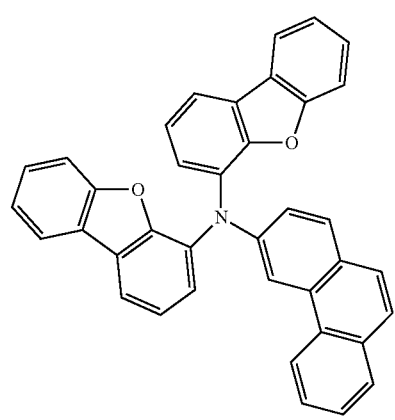
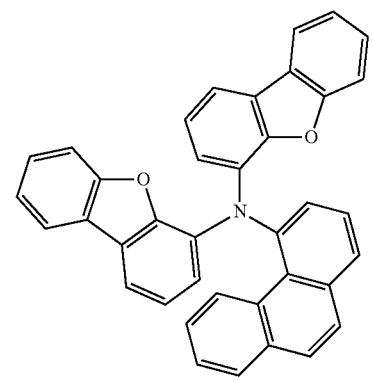
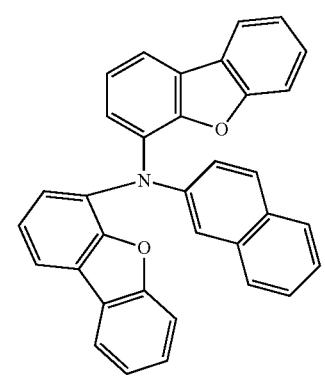
38
-continued
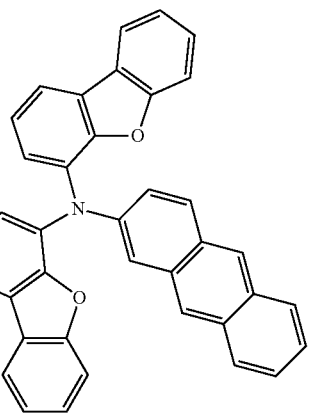
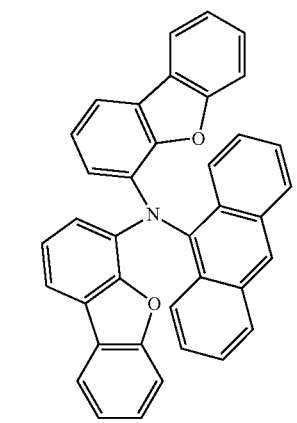
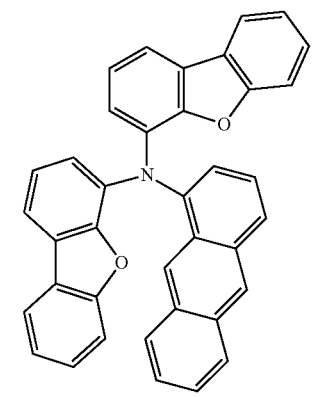
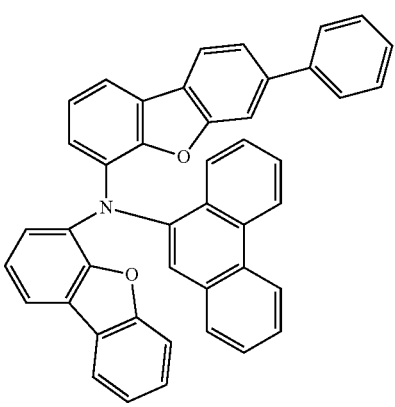

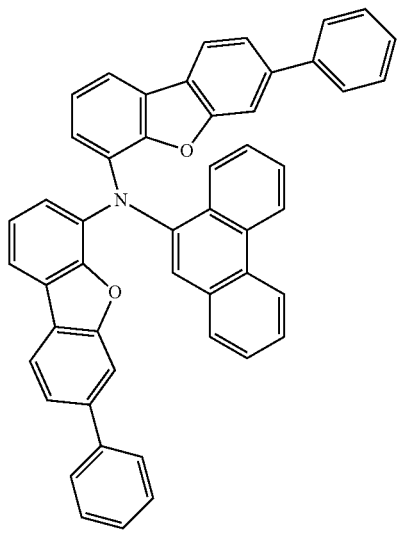
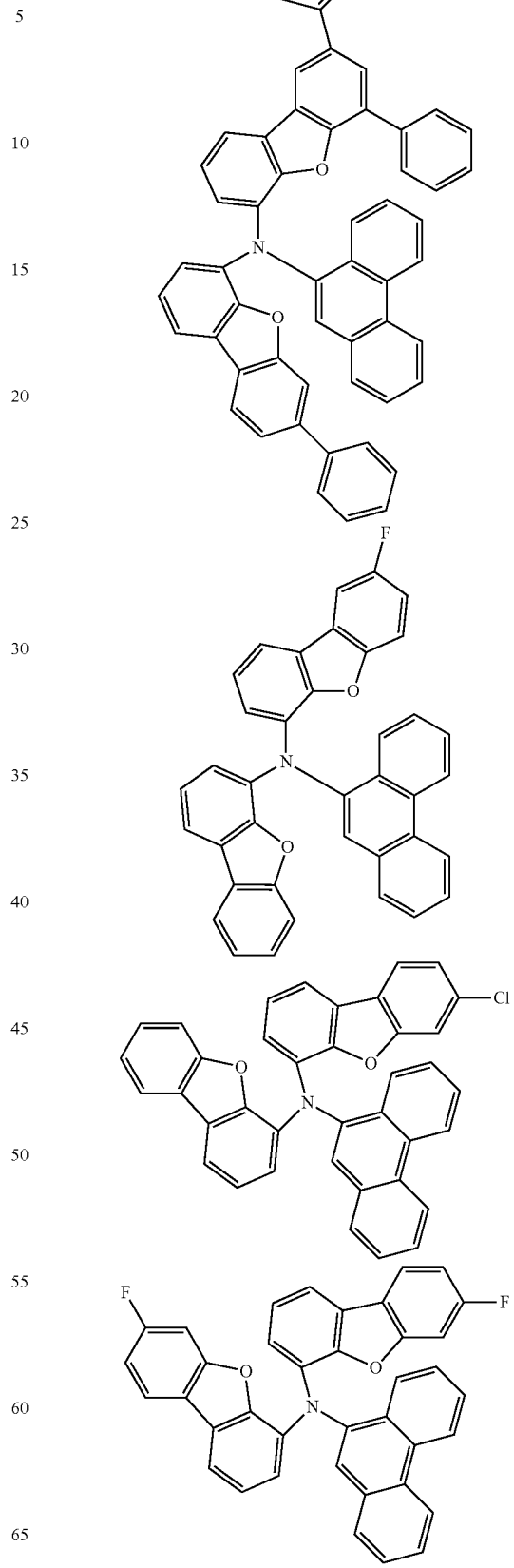

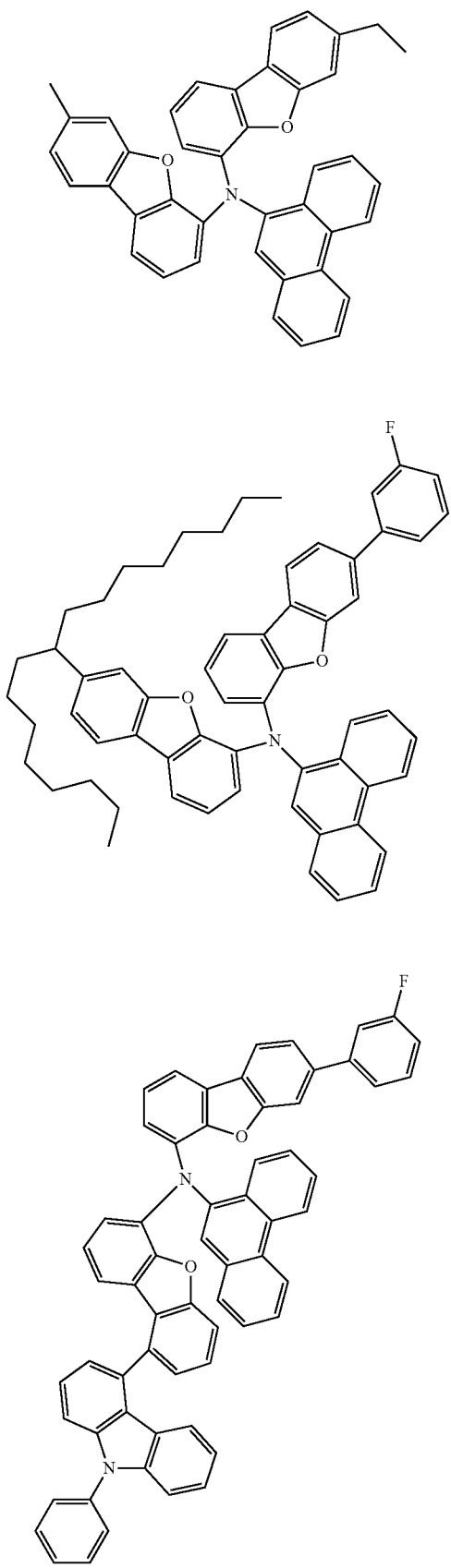
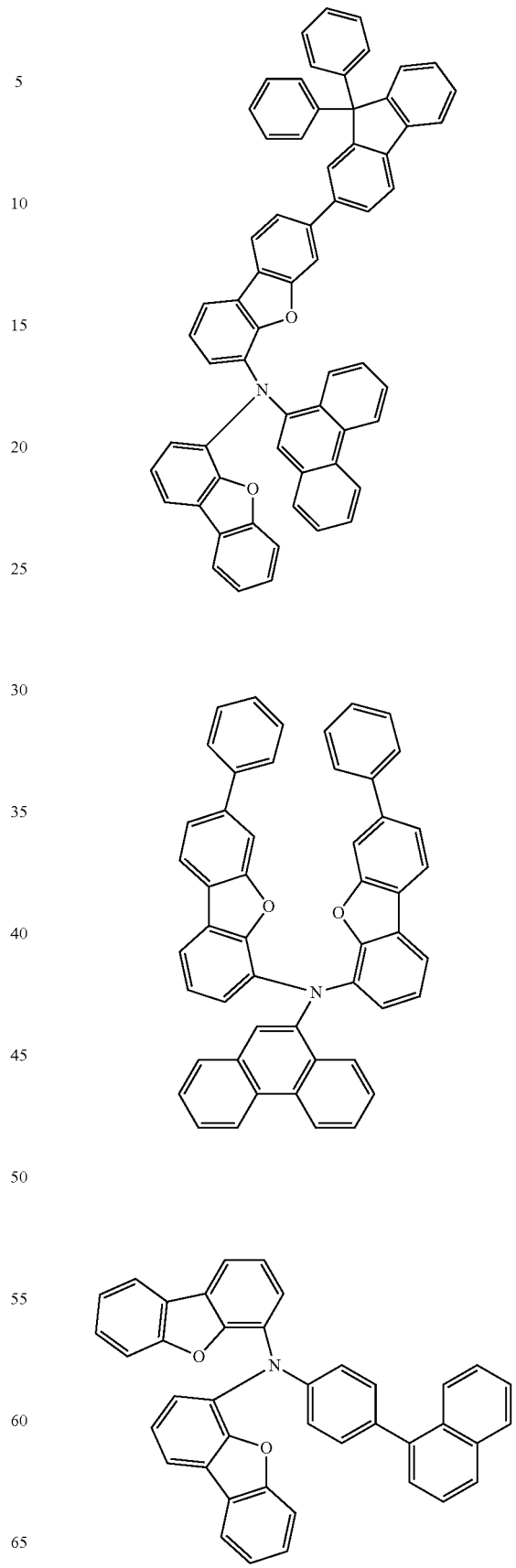

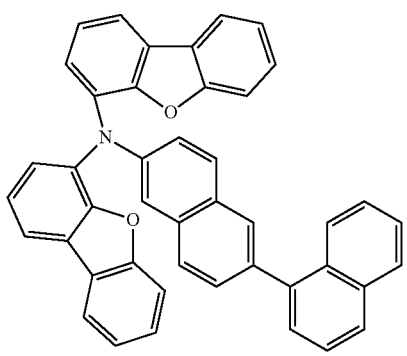

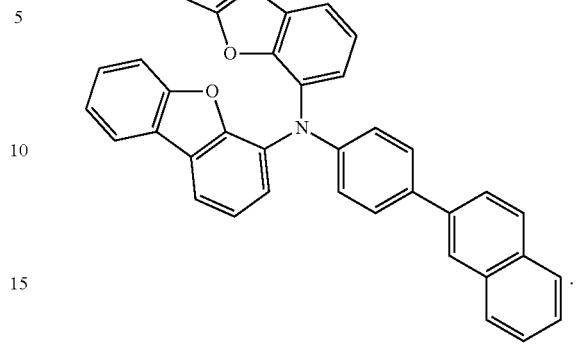

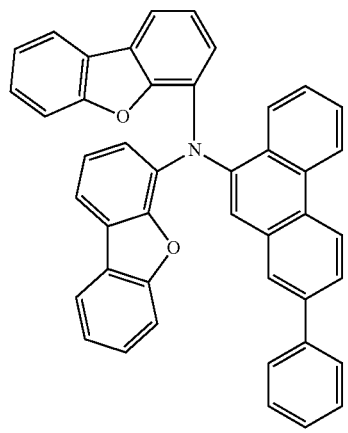

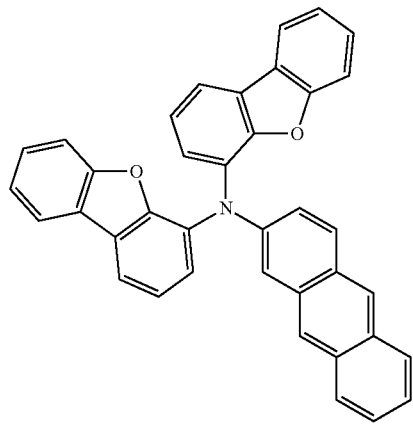 [SMILES: c1ccc2cc3cc(N(c4cccc5c4oc4ccccc45)c4cccc5c4oc4ccccc45)ccc3cc2c1]

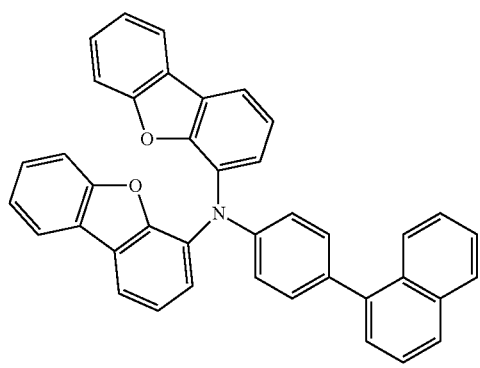 [SMILES: c1ccc2c(-c3ccc(N(c4cccc5c4oc4ccccc45)c4cccc5c4oc4ccccc45)cc3)cccc2c1]

5. An organic electroluminescent device comprising a material for an organic electroluminescent device including at least one monoamine compound represented by Formula I:

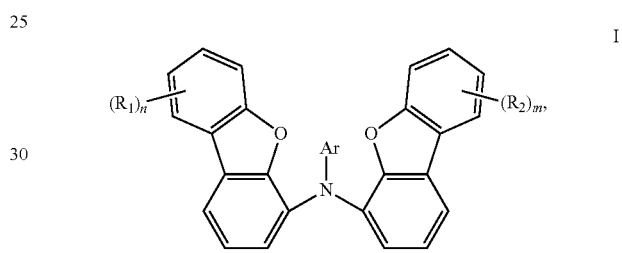

wherein in Formula I,
Ar is selected from a substituted or unsubstituted naphthyl group, a substituted or unsubstituted anthracenyl group, a substituted or unsubstituted phenanthrenyl group, a substituted or unsubstituted perylenyl group, a substituted or unsubstituted tetracenyl group, a substituted or unsubstituted naphthylphenyl group, a substituted or unsubstituted biphenylenyl group, a substituted or unsubstituted indenyl group, and a substituted or unsubstituted fluoranthenyl group,
$R_1$ and $R_2$ are each independently selected from a hydrogen atom, a halogen atom, an alkyl group having 1 to 15 carbon atoms, a substituted or unsubstituted aryl group having 6 to 30 carbon atoms for forming a ring, and a substituted or unsubstituted heteroaryl group having 1 to 30 carbon atoms for forming a ring,
n and m are each independently an integer selected from 1 to 4,
wherein a direct substituent of the substituted aryl group in Ar is selected from the group consisting of an alkyl group, an alkenyl group, a halogen atom, a silyl group, a cyano group, an alkoxy group, a nitro group, a hydroxyl group, a phenyl group, a naphthyl group, a biphenyl group, and a thiol group.

6. The organic electroluminescent device of claim 5, wherein the material is included in a hole transport layer.

7. The organic electroluminescent device of claim 5, wherein Ar is selected from a substituted or unsubstituted phenanthrenyl group and a substituted or unsubstituted naphthylphenyl group.

8. The organic electroluminescent device of claim 5, wherein the material is included in an emission layer.

9. The organic electroluminescent device of claim 5, wherein Ar comprises a substituted or unsubstituted phenanthrenyl group.
10. The organic electroluminescent device of claim 5, wherein the material is represented by at least one of the following compounds:
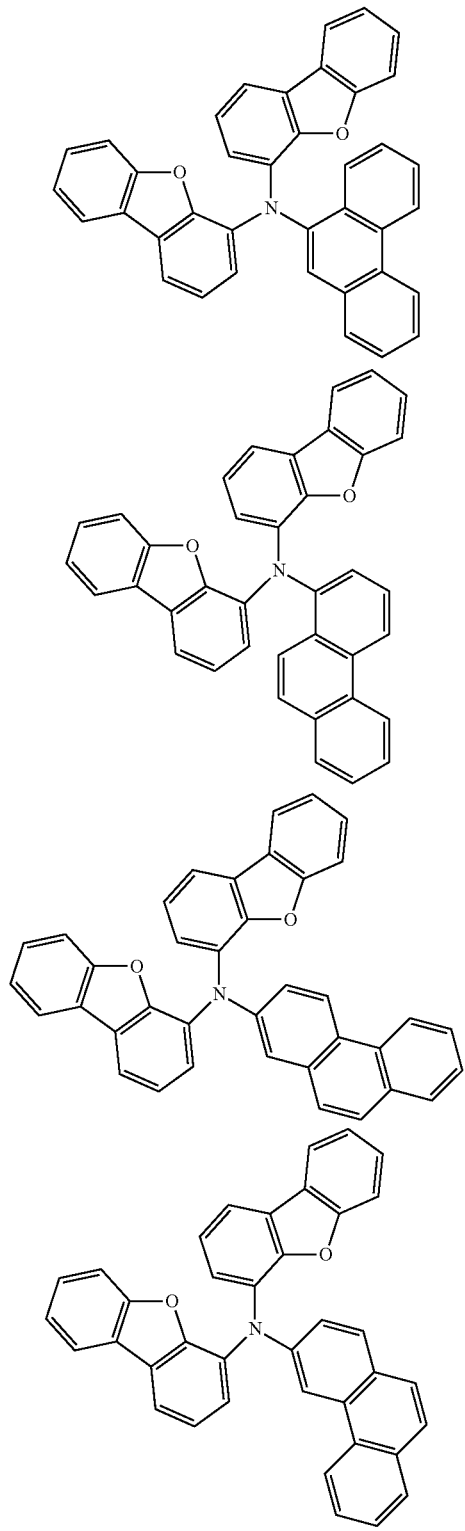
-continued
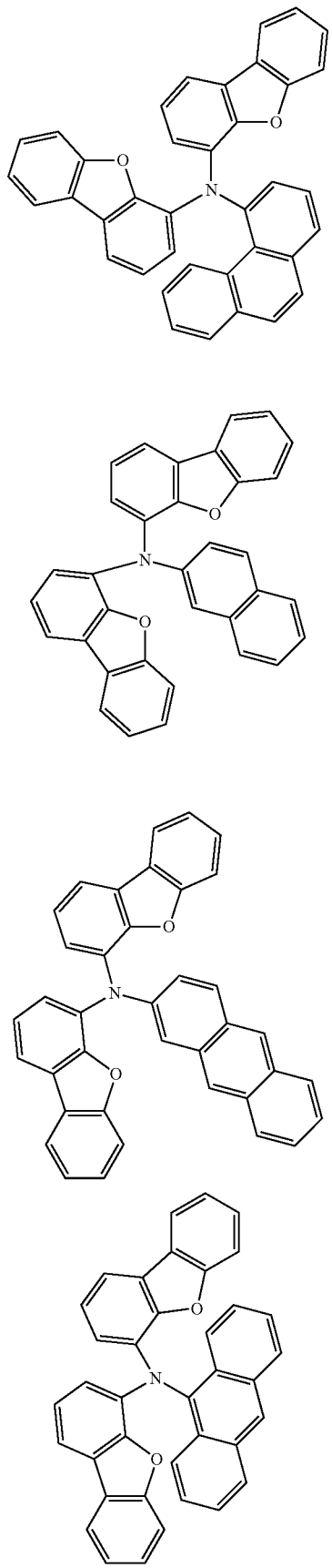

47
-continued
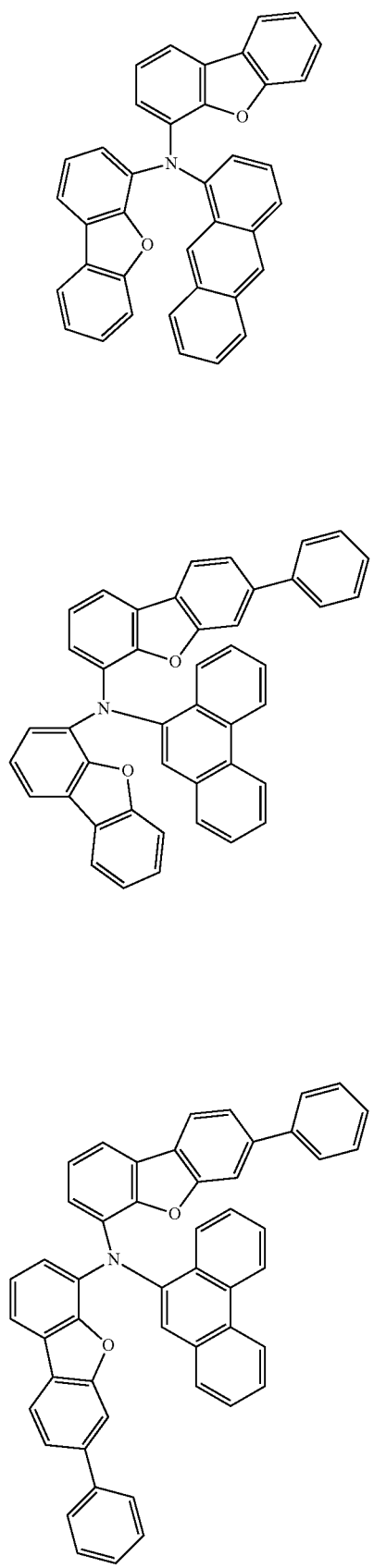
48
-continued
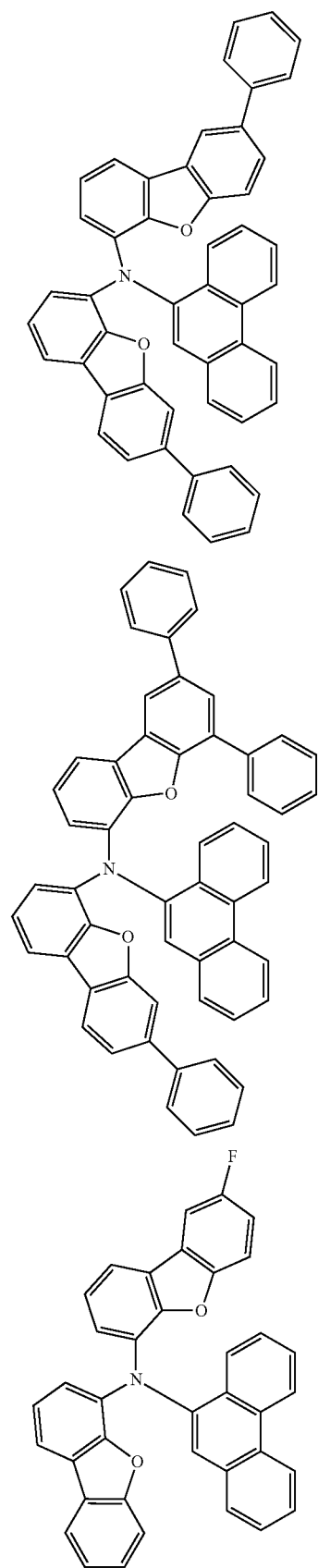

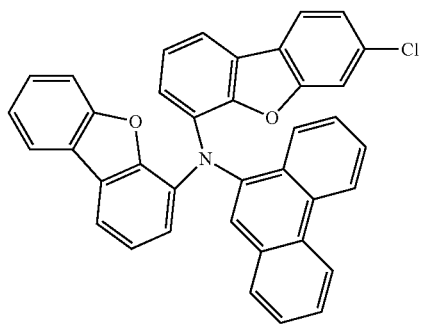
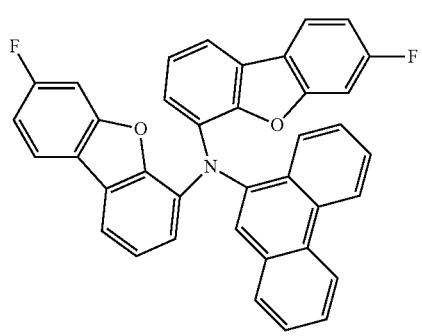
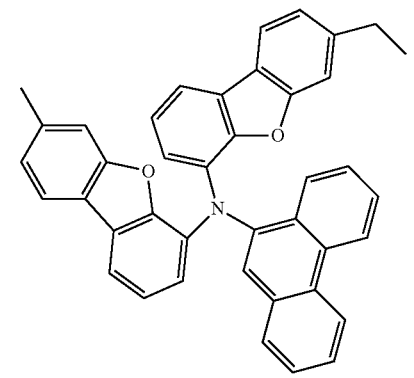 [SMILES: CCc1ccc2c(c1)oc1c(N(c3cc4ccccc4c4ccccc34)c3cccc4c3oc3cc(C)ccc34)cccc12]
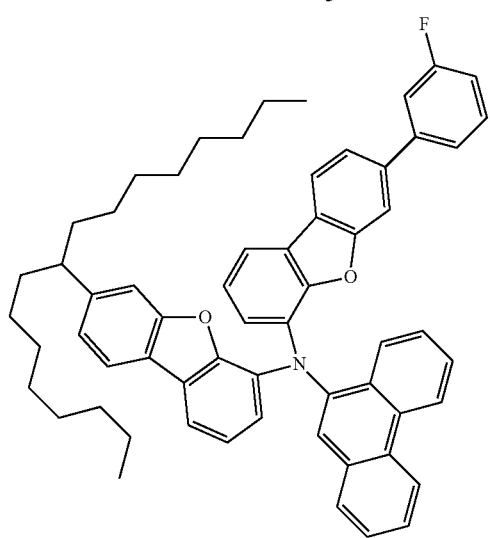
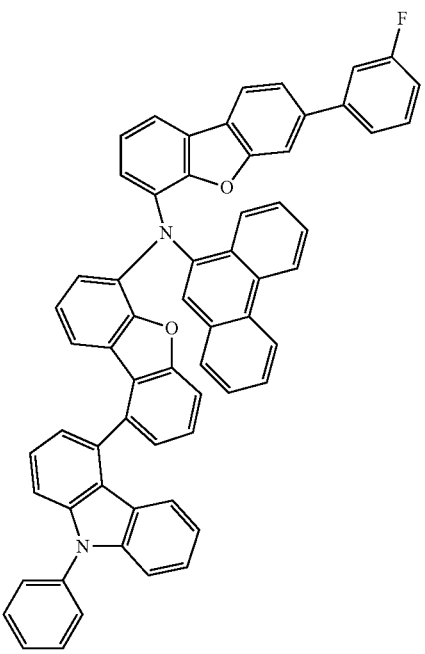
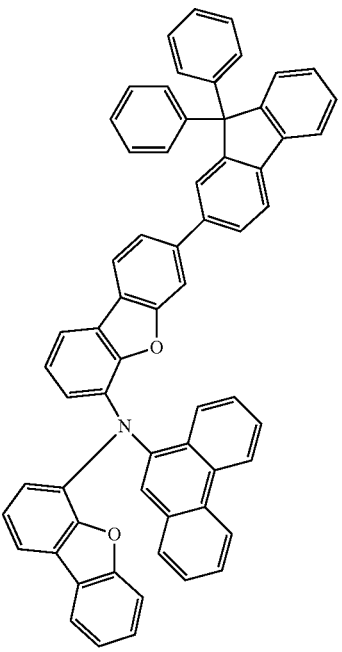 [SMILES: c1ccc(C2(c3ccccc3)c3ccccc3-c3ccc(-c4ccc5c(c4)oc4c(N(c6cc7ccccc7c7ccccc67)c6cccc7c6oc6ccccc67)cccc45)cc32)cc1]

51
-continued
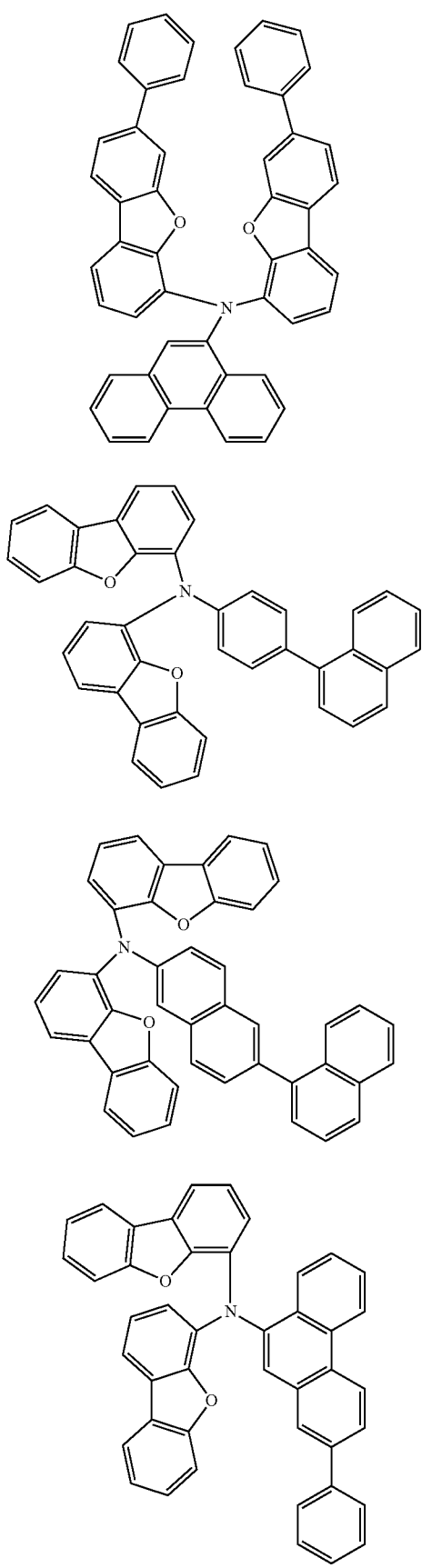
52
-continued
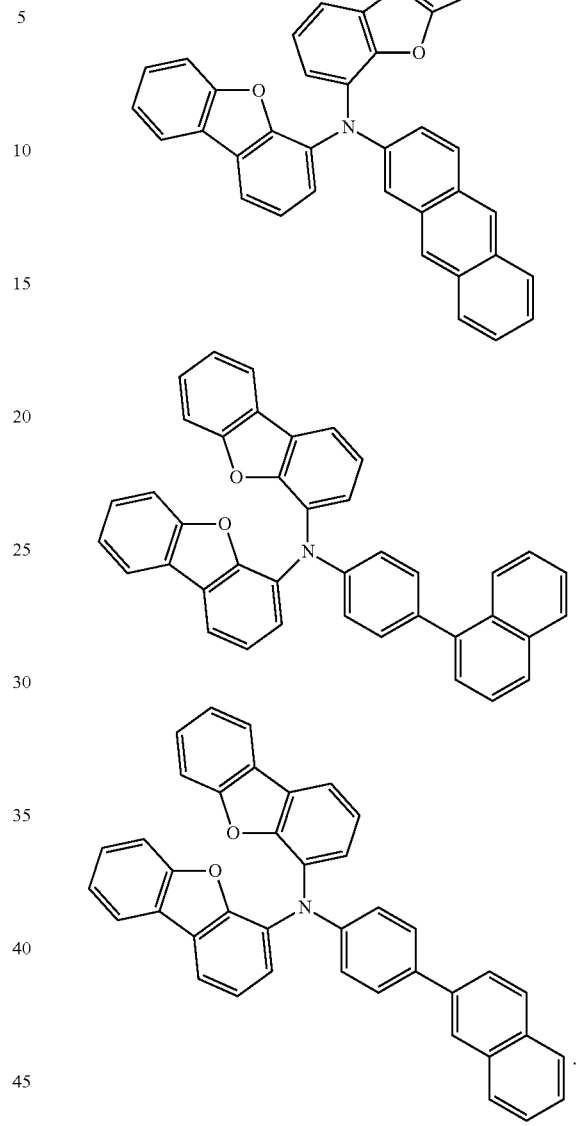
11. A material for an organic electroluminescent device, the material comprising at least one monoamine compound represented by Formula I:
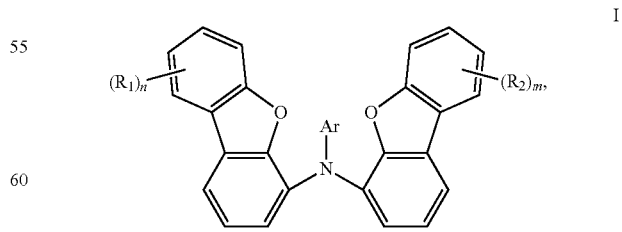
wherein in Formula I,
Ar is selected from a substituted or unsubstituted phenyl group, a substituted or unsubstituted naphthyl group, a substituted or unsubstituted anthracenyl group, a substituted or unsubstituted phenanthrenyl group, a substituted or unsubstituted perylenyl group, a substituted or unsubstituted tetracenyl group, a substituted or unsubstituted biphenyl group, a substituted or unsubstituted terphenyl group, a substituted or unsubstituted naphthylphenyl group, a substituted or unsubstituted biphenylenyl group, a substituted or unsubstituted indenyl group, a substituted or unsubstituted fluorenyl group, and a substituted or unsubstituted fluoranthenyl group, $R_1$ and $R_2$ are each independently selected from a hydrogen atom, a halogen atom, an alkyl group having 1 to 15 carbon atoms, a substituted or unsubstituted aryl group having 6 to 30 carbon atoms for forming a ring, and a substituted or unsubstituted heteroaryl group having 1 to 30 carbon atoms for forming a ring, provided that at least one of $R_1$ and $R_2$ is not hydrogen, n and m are each independently an integer selected from 1 to 4, wherein a direct substituent of the substituted Ar is selected from the group consisting of an alkyl group, an alkenyl group, a halogen atom, a silyl group, a cyano group, an alkoxy group, a nitro group, a hydroxyl group, a phenyl group, a naphthyl group, a biphenyl group, and a thiol group.

* * * * *